United States Patent
Robinson

(10) Patent No.: US 6,376,483 B1
(45) Date of Patent: Apr. 23, 2002

(54) BACTERIOCHLORINS AND BACTERIOPURPURINS USEFUL AS PHOTOSELECTIVE COMPOUNDS FOR PHOTODYNAMIC THERAPY AND A PROCESS FOR THEIR PRODUCTION

(75) Inventor: Byron C. Robinson, Santa Barbara, CA (US)

(73) Assignee: Miravant Pharmaceuticals, Inc., Santa Barbara, CA (US)

( * ) Notice: Subject to any disclaimer, the term of this patent is extended or adjusted under 35 U.S.C. 154(b) by 0 days.

(21) Appl. No.: 09/320,731

(22) Filed: May 27, 1999

(51) Int. Cl.$^7$ ................ A61K 31/409; C07D 487/22
(52) U.S. Cl. ............... 514/185; 514/410; 534/15; 534/16; 534/10; 540/145; 424/9.61
(58) Field of Search ................ 540/145; 514/185, 514/410; 534/10, 15, 16; 424/9.61

(56) References Cited

U.S. PATENT DOCUMENTS

| | | | |
|---|---|---|---|
| 4,649,151 A | 3/1987 | Dougherty et al. | 514/410 |
| 4,877,872 A | 10/1989 | Morgan et al. | 540/145 |
| 5,049,557 A | 9/1991 | Dori et al. | 514/185 |
| 5,051,415 A | 9/1991 | Morgan et al. | 514/185 |
| 5,109,129 A | 4/1992 | Morgan et al. | 540/145 |
| 5,171,749 A | 12/1992 | Levy et al. | 514/410 |
| 5,198,460 A | 3/1993 | Pandey et al. | 514/410 |
| 5,216,012 A | 6/1993 | Morgan et al. | 514/410 |
| 5,225,433 A | 7/1993 | Dougherty et al. | 514/410 |
| 5,236,915 A | 8/1993 | Fiel | 514/185 |
| 5,368,841 A | 11/1994 | Trauner et al. | 424/9 |
| 5,382,662 A | 1/1995 | Ellis, Jr. et al. | 540/145 |
| 5,399,583 A | 3/1995 | Levy et al. | 514/410 |
| 5,459,159 A | 10/1995 | Pandey et al. | 514/410 |
| 5,489,590 A | 2/1996 | Gulliya et al. | 514/224.8 |
| 5,504,075 A | 4/1996 | Burrows et al. | 514/189 |
| 5,512,675 A | 4/1996 | Tang et al. | 540/472 |
| 5,534,506 A | 7/1996 | Morgan et al. | 514/185 |
| 5,563,132 A | 10/1996 | Bodaness | 514/185 |
| 5,563,262 A | 10/1996 | Morgan et al. | 540/145 |
| 5,591,847 A | 1/1997 | Pandey | 540/472 |
| 5,648,485 A | 7/1997 | Dolphin et al. | 540/474 |
| 5,736,563 A | 4/1998 | Richter | 514/410 |

FOREIGN PATENT DOCUMENTS

WO    WO 97/32885    9/1997

OTHER PUBLICATIONS

Morgan et al., Chemical Abstracts, vol. 115:49207, 1991.*
Conant et al., Studies In The Chlorophyll Series. III. Products Of The Phase Test, 1930, J. Amer. Chem. Soc., 52:3013–3023.
Morgan et al., Observations On The Synthesis and Spectroscopic Characteristics Of Purpurins, 1986, J. Org. Chem, 51:1347–1350.
Morgan et al., Synthesis And In Vivo Photodynamic Activity of Some Bacteriochlorin Derivatives Against Bladder Tumors In Rodents, 1991, J. Medicinal Chemistry, 34:2126–2133.
Porphyrins and Metalloporphyrins, Table of Contents, 1975, ed. Kevin M. Smith, Elsevier 1975 N.Y.
The Porphyrins, Table of Contents, 1979, vol. I–VI, Ed D. Dolphin, Academic Press.
Willstatter et al., Investigations On Cholorphyll, 1928, Science Press Printing Company, Paper IX, 176–189.

* cited by examiner

Primary Examiner—Richard L. Raymond
(74) Attorney, Agent, or Firm—Finnegan, Henderson Farabow, Garrett & Dunner, L.L.P.

(57) ABSTRACT

Bacteriochlorins and bacteriopurpurins useful for photodynamic therapy and methods for their manufacture are described herein. Methods for producing the claimed compounds include contacting meso-diacrylate porphyrin precursors with a solvent and a base catalyst at sufficient temperature and time to yield the desired conversion. Reduced bacteriochlorins can be produced by contacting unsaturated bacteriochlorins or bacteriopurpurins with a hydrogenation catalyst and hydrogen. These methods provide new routes for synthesizing bacteriochlorins and bacteriopurpurins from symmetrical and asymmetrical meso-diacrylate porphyrins.

20 Claims, 3 Drawing Sheets

Figure 1:
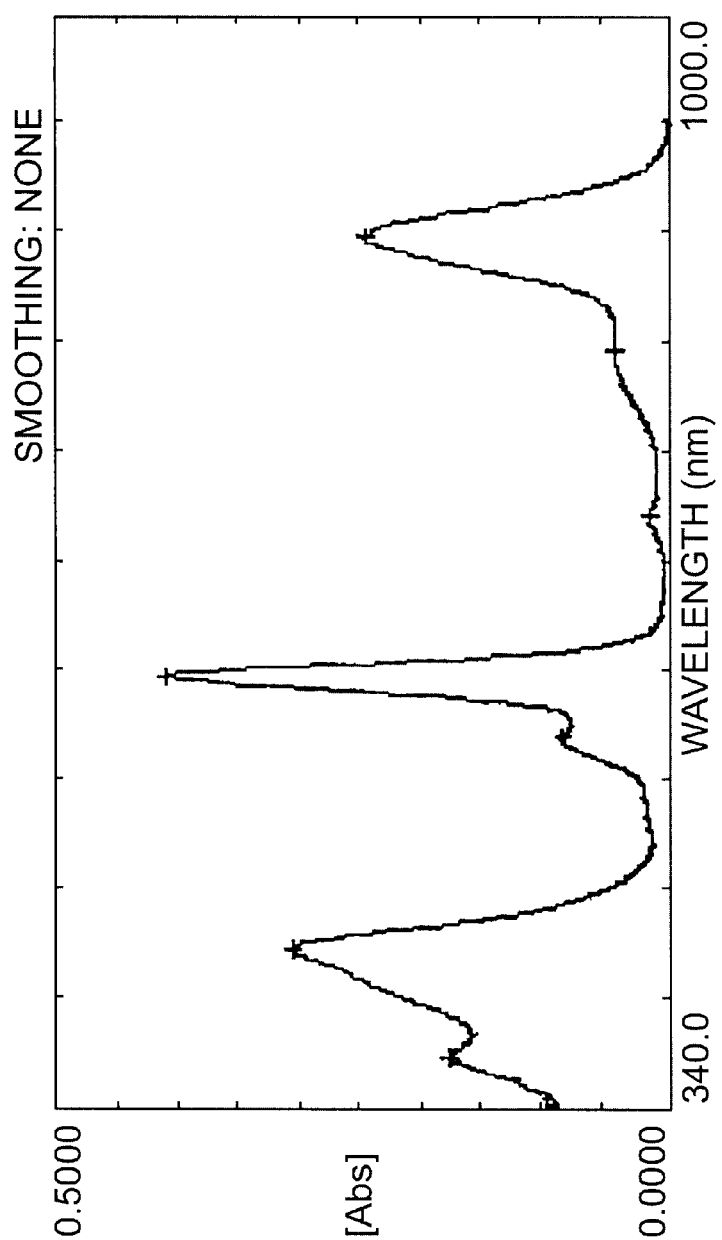

BACTERIOCHLORINS AND BACTERIOPURPURINS USEFUL AS PHOTOSELECTIVE COMPOUNDS FOR PHOTODYNAMIC THERAPY AND A PROCESS FOR THEIR PRODUCTION

FIELD OF THE INVENTION

The present invention relates to compounds useful as photoselective compounds in photodynamic therapy and a process for producing such compounds.

BACKGROUND OF THE INVENTION

Photodynamic therapy is a procedure that uses photoselective (light-activated) drugs to target and destroy diseased cells. Photoselective drugs transform light energy into chemical energy in a manner similar to the action of chlorophyll in green plants. The photoselective drugs are inactive until switched on by light of a specific wavelength thereby enabling physicians to target specific groups of cells and control the timing and selectivity of treatment. The result of this process is that diseased cells are destroyed with minimal damage to surrounding normal tissues.

Photodynamic therapy begins with the administration, to a patient, of a preferred amount of a photoselective compound which is selectively taken up and/or retained by the biologic target, i.e., tissue or cells. After the photoselective compound is taken up by the target, a light of the appropriate wavelength to be absorbed by the photoselective compound is delivered to the targeted area. This activating light excites the photoselective compound to a higher energy state. The extra energy of the excited photoselective compound can then be used to generate a biological response in the target area by interaction with oxygen. As a result of the irradiation, the photoselective compound exhibits cytotoxic activity, i.e., it destroys cells. Additionally, by localizing in the irradiated area, it is possible to contain the cytotoxicity to a specific target area. For a more detailed description of photodynamic therapy, see U.S. Pat. Nos. 5,225,433, 5,198,460, 5,171,749, 4,649,151, 5,399,583, 5,459,159, and 5,489,590, the disclosures of which are incorporated herein by reference.

One important factor in the effectiveness of photodynamic therapy for some disease indications is the depth of tissue penetration by the activating light. It would therefore be desirable to find photoselective compounds that absorb at wavelengths in which light penetration through the tissue is deep. Thus, there is a need for photoselective compounds, useful for photodynamic therapy, that possess long wavelength absorptions in the 750–850 nm range, a region where light penetration through tissues is optimal.

A large number of naturally occurring and synthetic dyes are currently being evaluated as potential photoselective compounds in the field of photodynamic therapy. Perhaps the most widely studied class of photoselective dyes in this field are the tetrapyrrolic macrocyclic compounds generally called porphyrins.

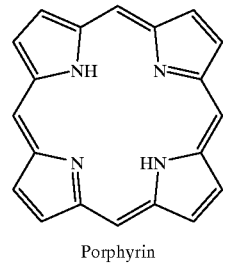

Porphyrin

Chlorins are compounds that differ from porphyrins in that one of the pyrrole rings has been reduced.

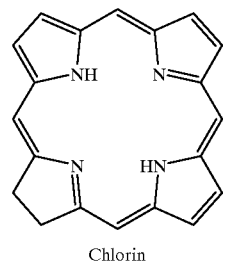

Chlorin

Bacteriochlorins, iso-bacteriochlorins, and bacteriopurpurins are a subclass of porphyrins in which two of the pyrrole rings have been reduced. Bacteriochlorins have opposing pyrrole rings reduced, and iso-bacteriochlorins have adjacent pyrrole rings reduced.

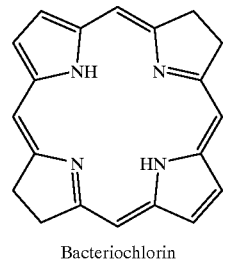

Bacteriochlorin

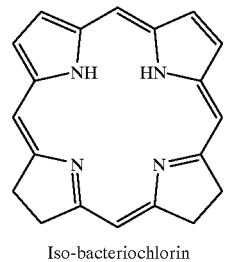

Iso-bacteriochlorin

Bacteriopurpurins differ from bacteriochlorins in that they have one or more 5-membered iso-cyclic rings fused to the macrocyclic ring.

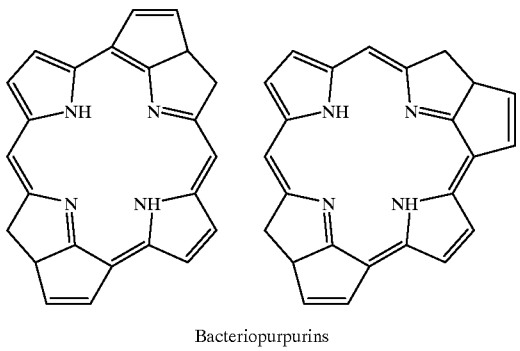

Bacteriopurpurins

Reduction of the pyrrolic rings in the porphyrin macrocycle has a pronounced effect on the absorption spectra of the reduced compounds. Bacteriochlorins and bacteriopurpurins have large band I absorptions that absorb light in the region of 720–850 nm. Thus, bacteriochlorins and bacteriopurpurins are classes of photoselective compounds that have great potential for use in photodynamic therapy.

Unfortunately, stable bacteriochlorins and bacteriopurpurins are notoriously difficult to synthesize from porphyrins or other chlorin intermediates. Many naturally occurring bacteriochlorins tend to be unstable in the presence of oxygen and light and are rapidly converted back to porphyrins and chlorins.

Accordingly, there is a need for stable photoselective compounds that absorb light at a wavelength where light penetration through tissues is optimal for specific disease indications.

More particularly, there is a need for a photoselective compound that absorbs light in the 750–850 nm range.

There is a further need for a process capable of producing stable bacteriochlorins and bacteriopurpurins.

SUMMARY OF THE INVENTION

To achieve the advantages and in accordance with the purpose of the invention, as embodied and broadly described herein, provided are bacteriochlorins of the following formulae:

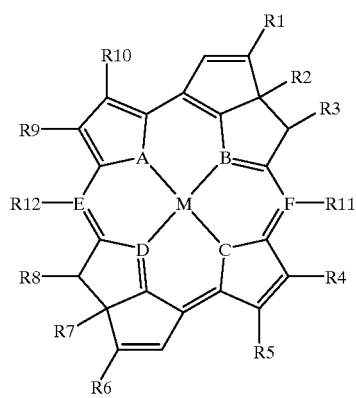

IA

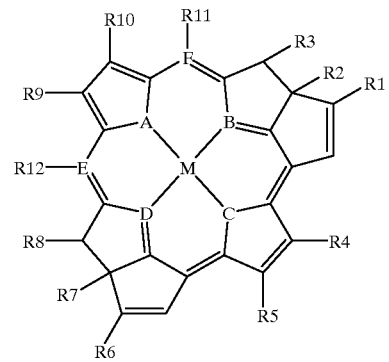

IB bacteriopurpurins of the following formulae:

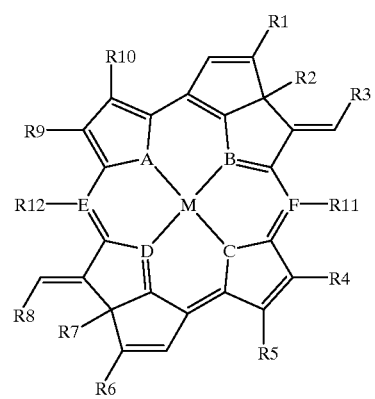

IIA

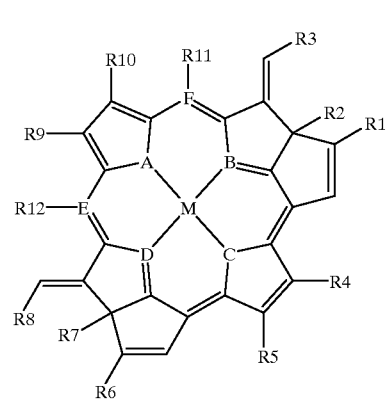

IIB and bacteriochlorins of the following formulae:

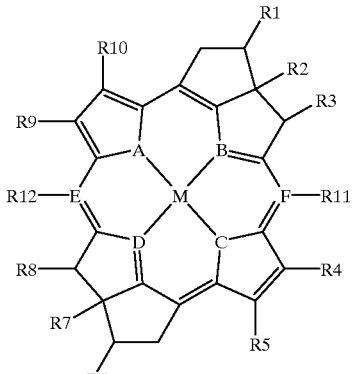

IIIA

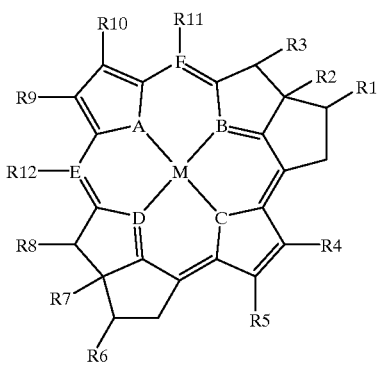

IIIB wherein in each of the above and following formulae:

$R_1$, $R_2$, $R_3$, $R_4$, $R_5$, $R_6$, $R_7$, $R_8$, $R_9$, $R_{10}$, $R_{11}$, and $R_{12}$ are independently sele from hydrogen, halogen atoms, unsubstituted or substituted alkyl, $C_3$–$C_6$ cycloalkyl, acetyl, aryl, alkenyl, alkynyl, amides, esters, $NR_{13}R_{14}$, CN, OH, $OR_{13}$, CHO, $(CH_2)_nOH$, $(CH_2)_nSH$, $(CH_2)_nO$-alkoxy, $(CH_2)_nSR_{13}$, $(CH_2)_nOR_{13}$, $(CH_2)_nCO_2R_{13}$, $(CH_2)_nCONHR_{13}$, $(CH_2)_nCON(R_{13})(R_{14})$, $CO_2R_{13}$, $CONHR_{13}$, $CONR_{13}R_{14}$, $SR_{13}$, $SO_3H$, $SO_3R_{13}$, $SO_2NHR_{13}$, $SO_2N(R_{13})(R_{14})$, and $SO_2N(R_{13})(R_{14})(R_{15})+X^-$;

$R_{13}$, $R_{14}$, and $R_{15}$ are independently selected from hydrogen, a physiologically acceptable salt, unsubstituted or substituted $C_1$–$C_6$ alkyl, aryl, alkenyl, or alkynyl, and a functional group having a molecular weight less than or equal to about 100,000 daltons;

n is an integer ranging from 1 to 4;

$R_{20}$ is an unsubstituted or substituted $C_1$–$C_6$ alkyl;

M is two hydrogens or a metal ion selected from Ag, Al, Ce, Co, Cr, Cu, Dy, Er, Eu, Fe, Gd, Hf, Ho, In, La, Lu, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr;

Also provided is a process for producing the compounds of formulae IA and IB comprising reacting the corresponding meso-acrylate porphyrin precursor in a solvent with a base catalyst for a time and at a temperature sufficient to form the compounds of formulae IA and IB:

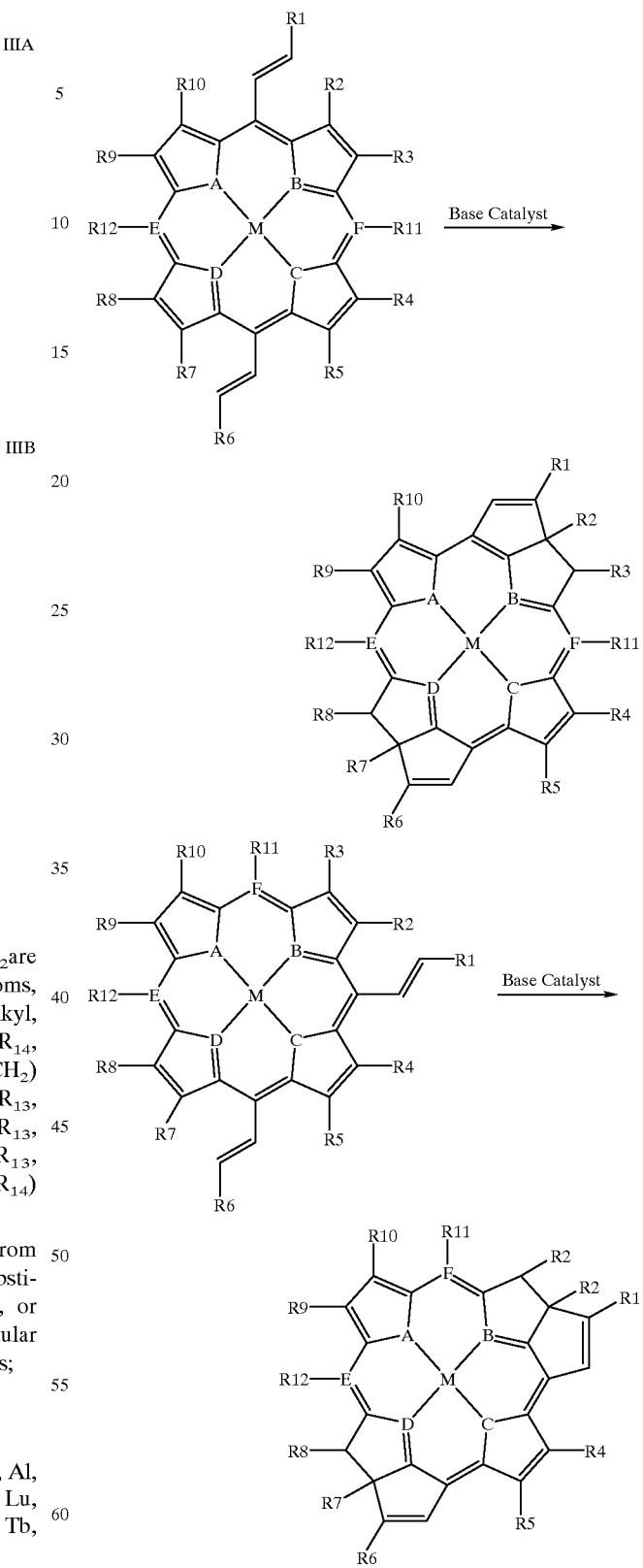

Another process is provided for producing the compounds of formulae IIA and IIB comprising reacting the corresponding meso-acrylate porphyrin precursor in a solvent with a base catalyst for a time and at a temperature sufficient to form the compounds of formulae IIA and IIB:

Furthermore, a process is provided for producing the compounds of formulae IIIA and IIIB comprising reacting the corresponding meso-acrylate porphyrin precursor in a solvent with hydrogen and a hydrogenation catalyst for a time and at a temperature sufficient to form the compound of formulae IIIA and IIIB:

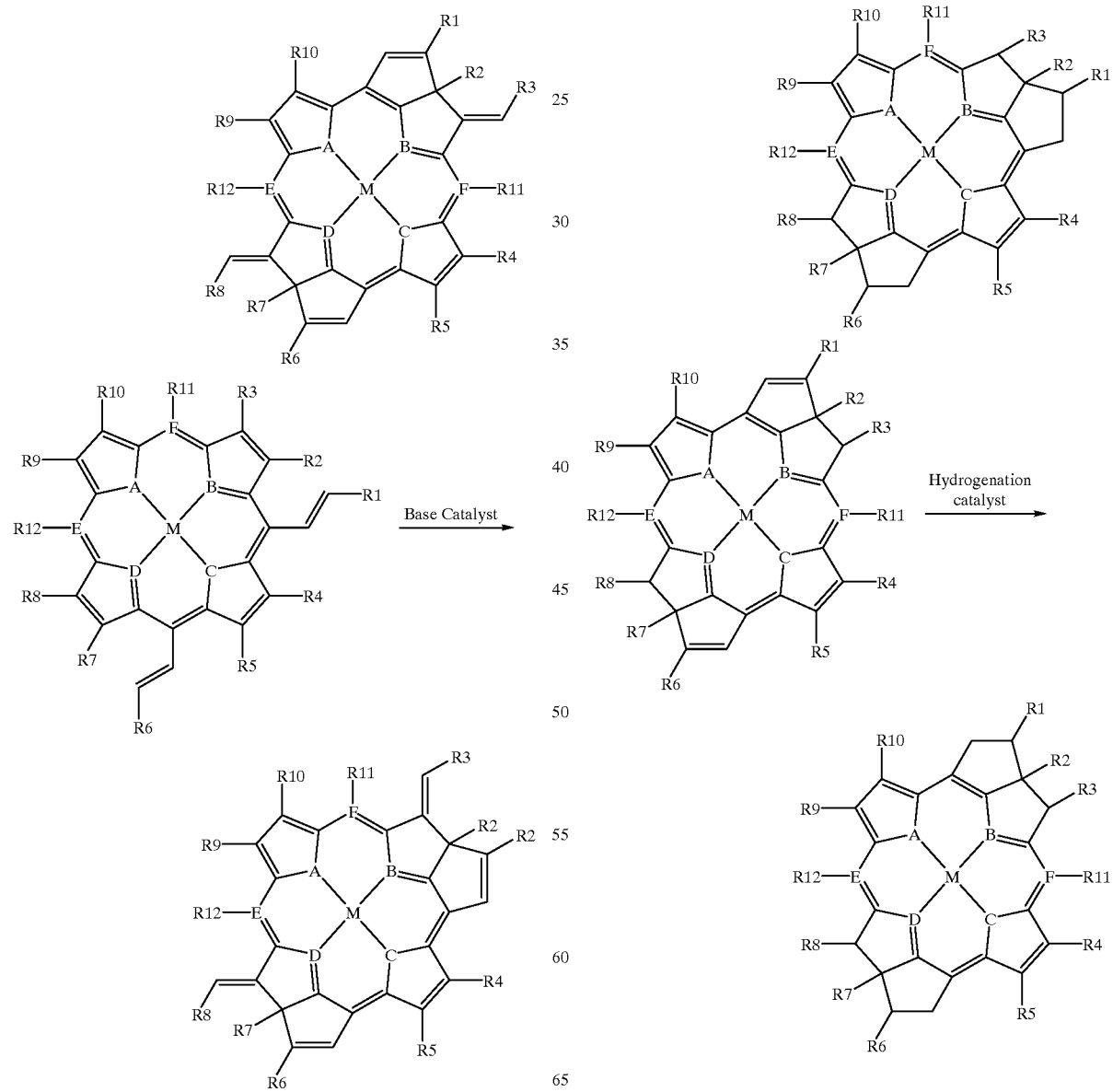

Selective hydrogenation and purification can also produce:

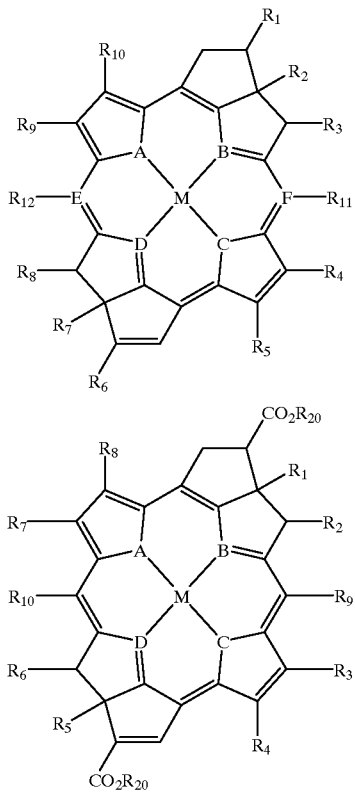

Additional advantages of the invention will be set forth in the detailed description which follows, and in part will be obvious from the description or may be learned by practice of the invention. The advantages of the invention can be realized and attained by means of the elements and combinations particularly pointed out in the appended claims.

The compounds of the present invention are useful for the photodiagnosis and phototherapy of tumor, cancer and malignant tissue (hereinafter referred to as "tumor").

When a human or animal having tumor is treated with doses of a compound of the present invention and when appropriate light rays or electromagnetic waves are applied, the compound emits light (i.e., it fluoresces). Thereby the existence, position and size of the tumor can be detected. This is called photodiagnosis.

When the tumor is irradiated with light of proper wavelength and intensity, the compound is activated to exert a cell killing effect against the tumor. This is called phototherapy.

Compounds intended for photodiagnosis and phototherapy ideally should have the following properties:

(a) non-toxic at normal therapeutic dosage unless and until activated by light;
(b) selectively photoactive;
(c) when light rays or electromagnetic waves are applied, they emit characteristic and detectable fluorescence;
(d) when irradiated with light rays or when electromagnetic waves are applied, they are activated to an extent sufficient to exert a cell killing effect against tumors; and
(e) easily metabolized or excreted after treatment.

The instant compounds can be used for diagnosis and the therapeutic treatment of a broad range of tumors. Examples of tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, cancer of the tongue, cerebral tumor, skin cancer, malignant goiter, prostatic cancer, cancer of the parotid gland, Hodgkin's disease, multiple myeloma, renal cancer, leukemia, and malignant lymphocytoma. For diagnosis, the sole requirement is that the tumor be capable of selectively fluorescing when exposed to proper light. For treatment, the tumor must be penetratable by the activation energy. For diagnosis, light of shorter wavelength is used whereas for therapeutic purposes light of longer wavelength is used to permit ready penetration of the tumor tissue.

It is necessary that the light rays have sufficient intensity to cause the compounds to emit fluorescence for diagnosis and to exert a cell killing effect for therapy.

The compounds of the present invention are also useful for the treatment of opthalmological disorders such as age-related macular degeneration and choroidal neovascularization; dermatological disorders such as psoriasis; gynecological disorders such as dysfunctional uterine bleeding; urological disorders such as condyloma virus; cardiovascular disorders such as restenosis and atherosclerotic plaques; and for hair removal.

The source of irradiation for photodiagnosis and phototherapy is not restricted, but a laser beam is preferable because intensive light rays in a desired wavelength range can be selectively applied. For example, in photodiagnosis, the compound of the invention is administered to a human or animal body, and after a certain period of time, light rays are applied to the part to be examined. When an endoscope can be used for the affected part, such as lungs, gullet, stomach, womb, urinary baldder or rectum, it is irradiated using the endoscope, and the tumor portion selectively emits fluorescence. This portion is observed visually, or observed through an adapted fiber scope by eye or on a CRT screen.

In phototherapy, after administration of the dosage, the irradiation is carried out by laser light from the tip of quartz fibers. Besides the irradiation of the surface of the tumor, the internal part of the tumor can be irradiated by inserting the tip of quartz fibers into the tumor. The irradiation can be visually observed or imaged on a CRT screen.

For photodiagnosis, light of wavelength between 360 and 760 nm. is suitable for activating the present tetrapyrrole compounds. Of course, each compound has a specific optimal wavelength of activation. A long wavelength ultraviolet lamp is particularly suitable for photodiagnosis. Similar methods for viewing the treated tumor can be used as already described for phototherapy.

DETAILED DESCRIPTION OF THE INVENTION

Reference will now be made in detail to the presently preferred embodiments of the present invention.

In accordance with the invention, as embodied and broadly described herein, bacteriochlorins and bacteriopurpurins are provided that are particularly useful as photoselective compounds in photodynamic therapy. The present invention is directed to bacteriochlorins of formulae IA and IB, bacteriopurpurins of formulae IIA and IIB, and bacteriochlorins of formulae IIIA and IIIB as described above.

In accordance with the invention, as embodied and broadly described herein, the present inventors surprisingly discovered that the bacteriochlorins and bacteriopurpurins of the invention can be successfully produced by cyclization of meso-diacrylate porphyrins or by hydrogenation of bacteriopurpurins in the presence of a hydrogenation catalyst.

To obtain the desired final product, the corresponding meso-acrylate porphyrin is used as the precursor compound.

Accordingly, the present invention also relates to a process for producing bacteriochlorins and bacteriopurpurins of the formulae IA, IB, IIA, IIB, IIIA, or IIIB. The process involves reacting the corresponding meso-diacrylate porphyrin precursor compound in a solvent and a base catalyst for a time and temperature sufficient to form compounds of formulae IA, IB, IIA, IIB, IIIA, or IIIB.

The chemistry of purpurins and the cyclization of meso-acrylate porphyrins to form purpurins are well published in the literature. The tetrapyrroles can be prepared by various synthetic methods which are found in the literature, e.g., Chlorin $e_6$ Willstatter, R., Stoll, A.; *Investigations on Chlorophyll*, (Trans., Schertz, F. M., Merz, A. R.,) p. 176. Science Printing Press, Lancaster, Pa., 1928.
Willstatter, R., Isler, M.; *Ann. Chem.*, 390, 269 (1912).
Fisher, H., Baumler, R.; *Ann. Chem.*, 474, 65 (1929).
Fisher, H., Siebel, H.; *Ann. Chem.*, 499, 84 (1932).
Conant, J. B., Mayer, W. W.; *J. Amer. Chem. Soc.*, 52, 3013 (1930).

Chlorin $e_6$, $e_4$, Mesochlorin $e_6$, Bacteriochlorin $e_6$

Fischer and Orth, "Des Chemie des Pyrrole" Akademische Verlazsgesellschaft, Leipzig, 1940, Vol. 11, Part 2.

General Reference for Porphyrins

"Porphyrins and Metalloporphyrins" ed. Kevin M. Smith, Elsevier 1975 N.Y.

Patents by Morgan (U.S. Pat. Nos. 4,877,872; 5,051,415; 5,109,129; 5,216,012; and 5,534,506 for example) outline procedures for the synthesis of purpurins. Previous attempts to form bacteriopurpurins from diacrylate porphyrins were unsuccessful (e.g., Morgan, A. R. et al., J. of Medicinal Chemistry, 34, 1991, 2126, 2128). In studies on the mechanisms of cyclization of meso-acrylate porphyrins, the present inventor has demonstrated that a variety of base catalysts efficiently convert meso-acrylate porphyrins to purpurins. Based on the success of base catalyzed cyclization reactions, the cyclization of bis-acrylate porphyrins was investigated in the hope of generating synthetic bacteriopurpurins with long wavelength absorptions for use as photodynamic reagents in photodynamic therapy. Schemes 1 and 2 outline the chemistry involved in the synthesis of bacteriopurpurins.

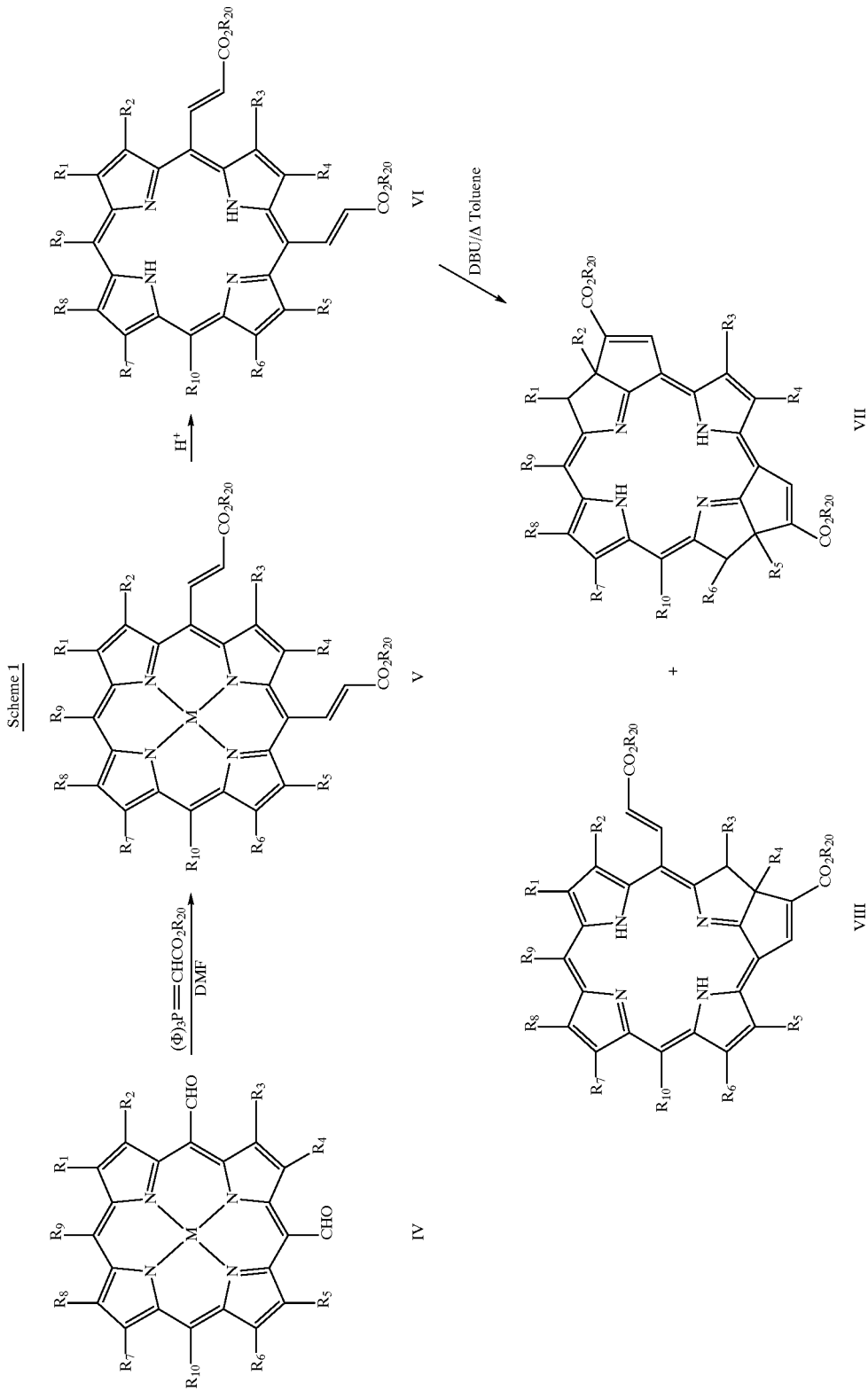

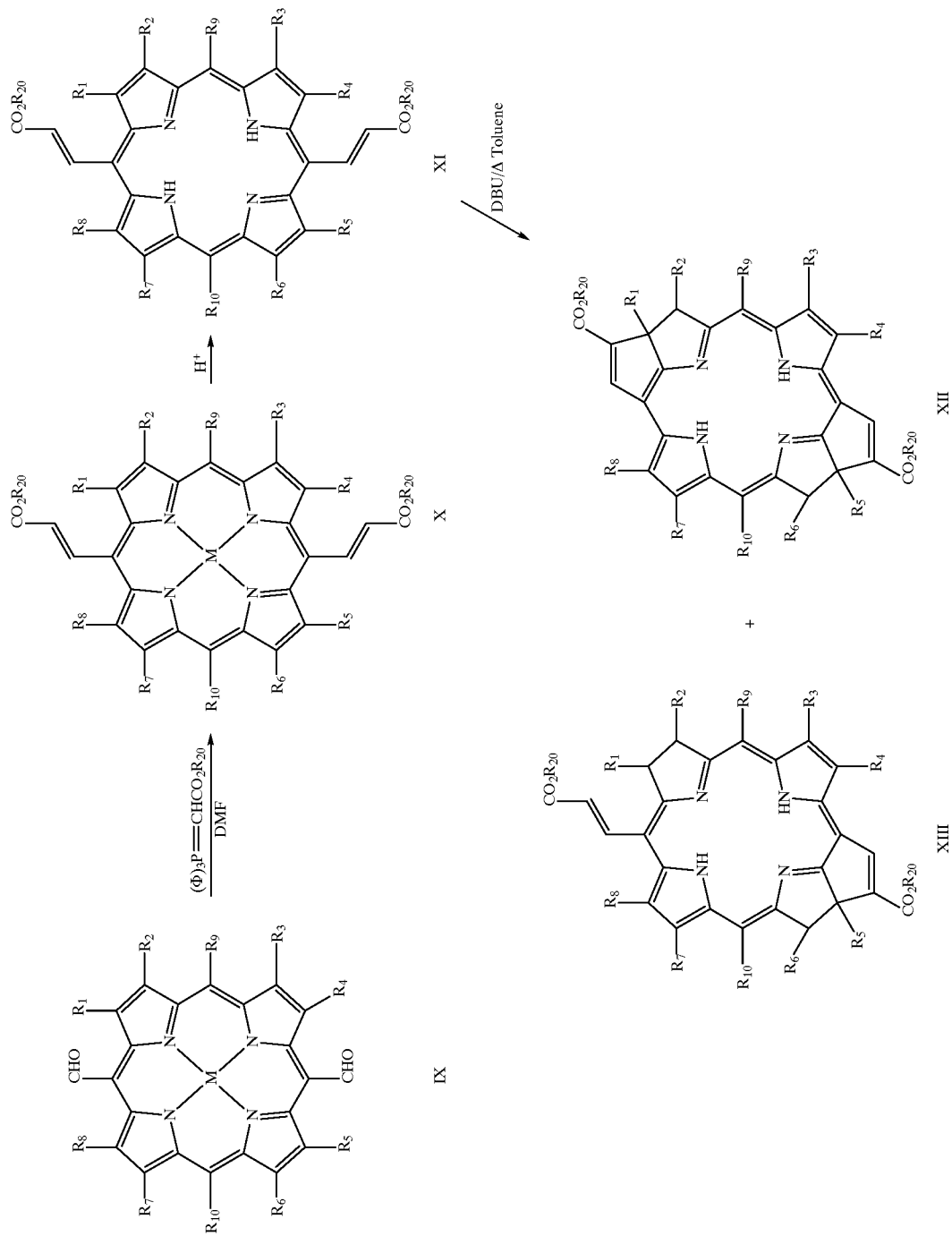

Porphyrins of formula XIV and XV

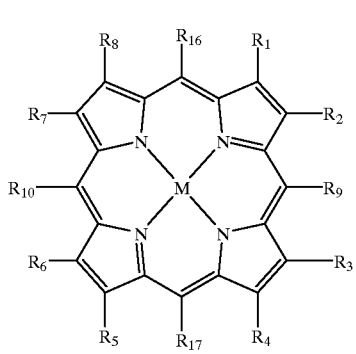

XIV

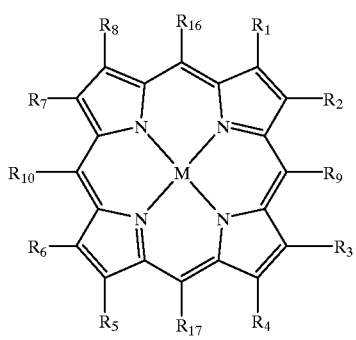

XV

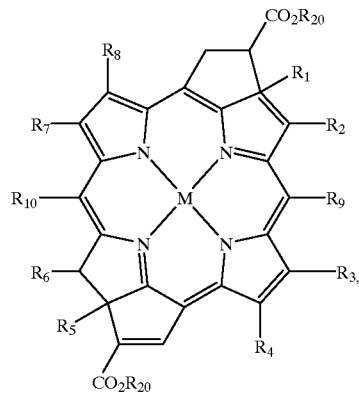

may be used to prepare the compounds outlined in schemes 1 and 2 wherein $R_1$, $R_2$, $R_3$, $R_4$, $R_5$, $R_6$, $R_7$, $R_8$, $R_9$, $R_{10}$, $R_{16}$, and $R_{17}$ are independently selected from hydrogen, halogen atoms, unsubstituted or substituted alkyl, $C_3$–$C_6$ cycloalkyl, acetyl, aryl, alkenyl, alkynyl, amides, esters, $NR_{13}R_{14}$, CN, OH, $OR_{13}$, CHO, $(CH_2)_nOH$, $(CH_2)_nSH$, $(CH_2)_nO$-alkoxy, $(CH_2)_nSR_{13}$, $(CH_2)_nOR_{13}$, $(CH_2)_nCO_2R_{13}$, $(CH_2)_nCONHR_{13}$, $(CH_2)_nCON(R_{13})(R_{14})$, $CO_2R_{13}$, $CONHR_{13}$, $CONR_{13}R_{14}$, $SR_{13}$, $SO_3H$, $SO_3R_{13}$, $SO_2NHR_{13}$, $SO_2N(R_{13})(R_{14})$, and $SO_2N(R_{13})(R_{14})(R_{15})+X^-$;

$R_{13}$, $R_{14}$, and $R_{15}$ are independently selected from hydrogen, a physiologically acceptable salt, unsubstituted or substituted $C_1$–$C_6$ alkyl, aryl, alkenyl, or alkynyl, and a functional group having a molecular weight less than or equal to about 100,000 daltons;

and n is an integer ranging from 1 to 4;

$R_{20}$ is a substituted or unsubstituted $C_1$–$C_6$ alkyl;

A, B, C, D, E, and F are independently selected from C, S, N, $N^+(R_{16})X^-$, O, Se, and Te; wherein $R_{16}$ is a functional group having a molecular weight less than or equal to about 100,000 daltons and X is a charge balancing ion;

and wherein M is selected from two hydrogens or a metal ion selected from Ag, Al, Ce, Co, Cr, Cu, Dy, Er, Eu, Fe, Gd, Hf, Ho, In, La, Lu, Mn, Mo, Ni, Nd, Pb, Pd, Pr, Pt, Rh, Sb, Sc, Sm, Sn, Tb, Th, Ti, Tl, Tm, U, V, Y, Yb, Zn, and Zr.

Furthermore, selective hydrogenation and purification can provide:

In a preferred embodiment, meso-diformyl porphyrins may be reacted with the appropriate Wittig reagent to form meso-diacrylate porphyrins. Alternatively, the methodology of Morgan and co-workers may be used whereby Ni-5-formyl-10-acrylate porphyrins (1) and Ni-5-formyl-15-acrylate porphyrins (2) may be reacted with the Wittig reagent to form Ni-5, 15-bis-acrylate (3) and the Ni-5, 10-bis-acrylate (9) porphyrins. Demetallation of these porphyrins with sulfuric acid gives the desired free base diacrylate analogs. In the present invention, both synthetic routes to the formation of meso-diacrylate porphyrins were used. Examples of the types of porphyrins used in the invention are shown below.

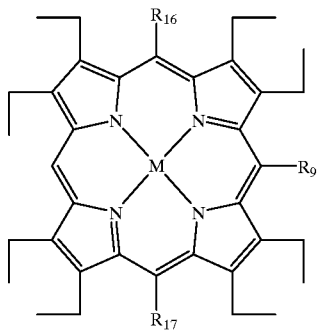

(1) $R_{16}$ = CHO, $R_9$ = CHCHCO$_2$Et, $R_{17}$ = H
(2) $R_{16}$ = CHO, $R_9$ = H, $R_3$ = CHCHCO$_2$Et
(3) $R_{16}$ = $R_{17}$ = CHCHCO$_2$Et, $R_9$ = H
(5) M = H2, $R_{16}$ = $R_9$ = CHCHCO$_2$Et, $R_{17}$ = H
(6) M = H2, $R_{16}$ = $R_{17}$= CHCHCO$_2$Et, $R_9$ = H

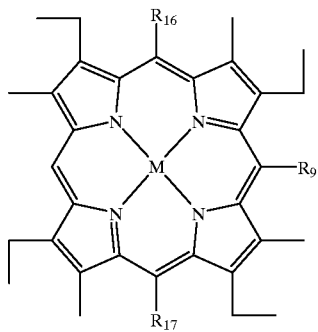

-continued
(7) $R_{16}$ = CHO, $R_9$ = CHO, $R_{17}$ = H
(8) $R_{16}$ = CHO, $R_9$ = H, $R_{17}$ = CHO
(9) $R_{16}$ = $R_2$ = CHCHCO$_2$Et, $R_{17}$ = H
(10) $R_{16}$ = $R_3$ = CHCHCO$_2$Et, $R_9$ = H
(11) M = H2, R1 = $R_9$ = CHCHCO$_2$Et, $R_{17}$ = H
(12) M = H2, R1 = $R_{17}$= CHCHCO$_2$Et, $R_9$ = H In preferred embodiments, M is nickel for compounds 1–3 and 7–10. The synthesis of bacteriopurpurins was achieved by cyclization of the demetallated meso-diacrylate porphyrins (5, 6, 11, 12) in refluxing toluene/DBU under an argon atmosphere. In addition to the desired bacteriopurpurins, minor polar bands were also isolated and these proved to be the 15-acrylate purpurins shown in Schemes 3 and 4. A variety of base catalysts may be used to effect the cyclization reactions. These include 1,8-diazobicyclo[5.4.0]undec-7-ene (DBU), 1,5-diazobicyclo [4.3.0]-5-nonene (DBN), 1,4-diazabicyclo[2.2.2]octane (DABCO), 1,1,3,3-tetramethylguanidine, and pyrrolidine. The preferred basic catalyst is 1,8-diazobicyclo[5.4.0] undec-7-ene (DBU). Any suitable solvent can be used provided that it has appropriate solubility characteristics. Examples of solvents that can be used include, for example, toluene and benzene. Toluene is preferred. The temperature to which the reaction mixture is heated generally ranges from about 100° C. to about 160° C. The reaction time preferably ranges from about 2 hours to about 24 hours.

Figure 2:
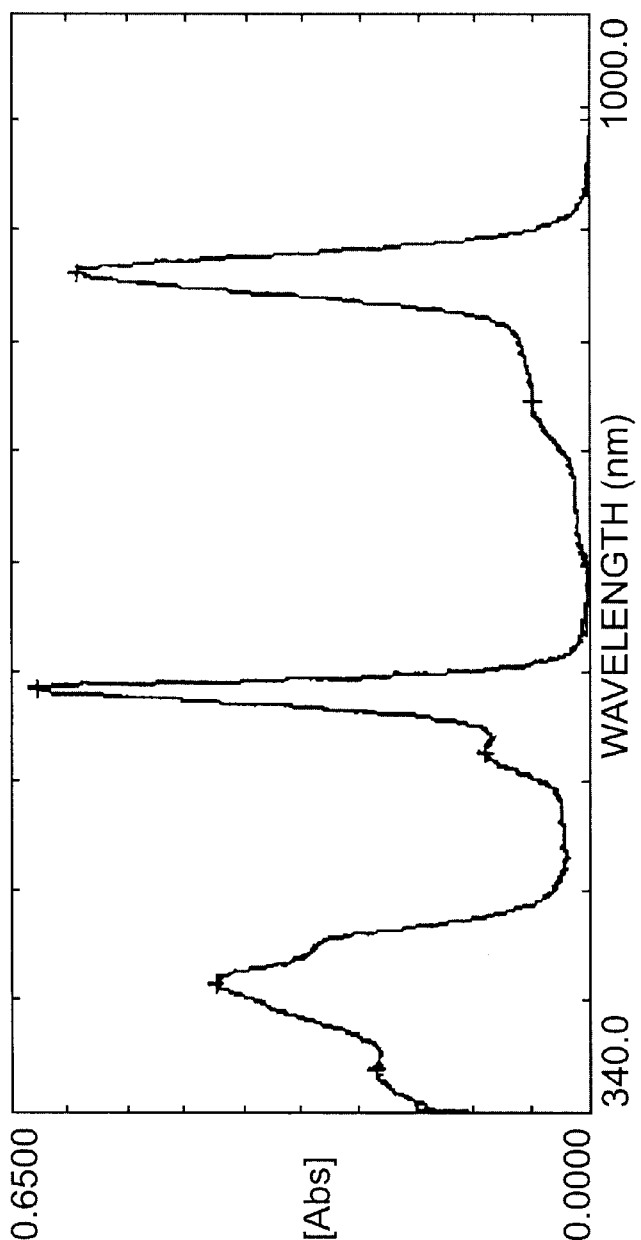
Figure 3:
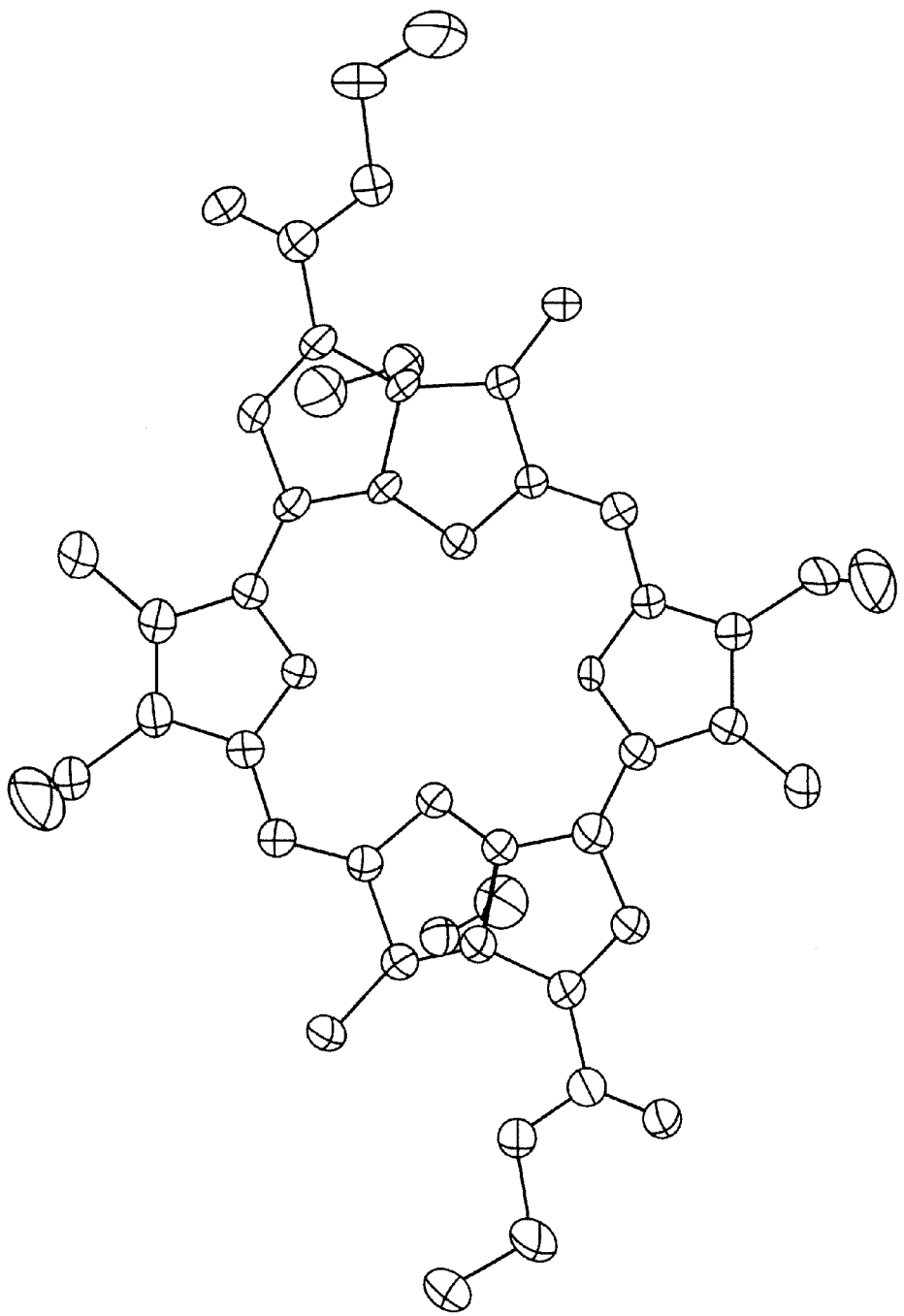

The UV/Visible absorption spectra of compounds 13b(R= Et) and 14b(R=Me) are shown in FIGS. 1 and 2. FIG. 3 shows an X-ray crystal structure of 14b(R=Me). In general bacteriopurpurins of these types display prominent band I absorption at ~850–860 nm, a sharp absorption band at ~599 nm and a broad Soret absorption band at ~380 nm.

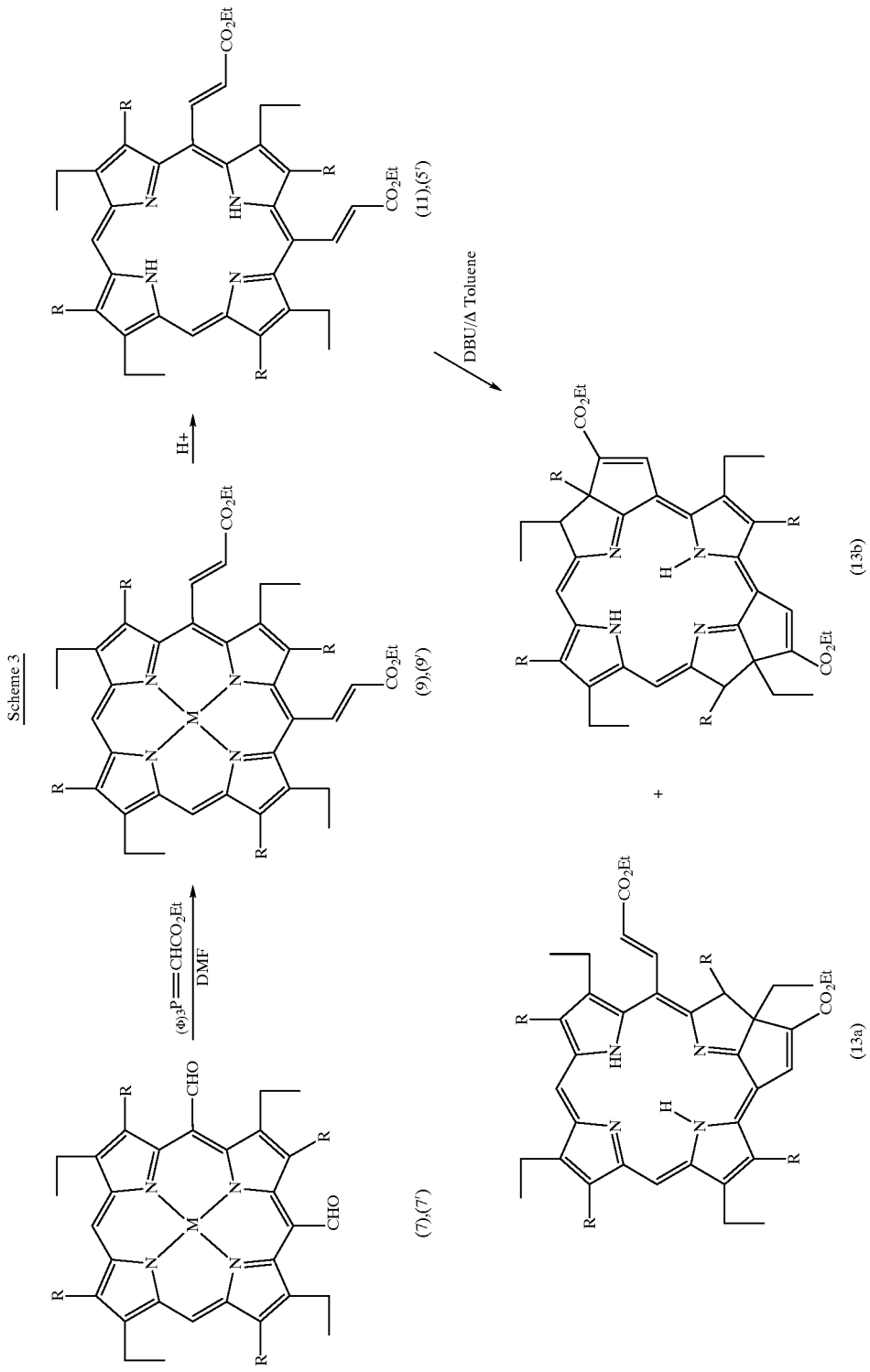

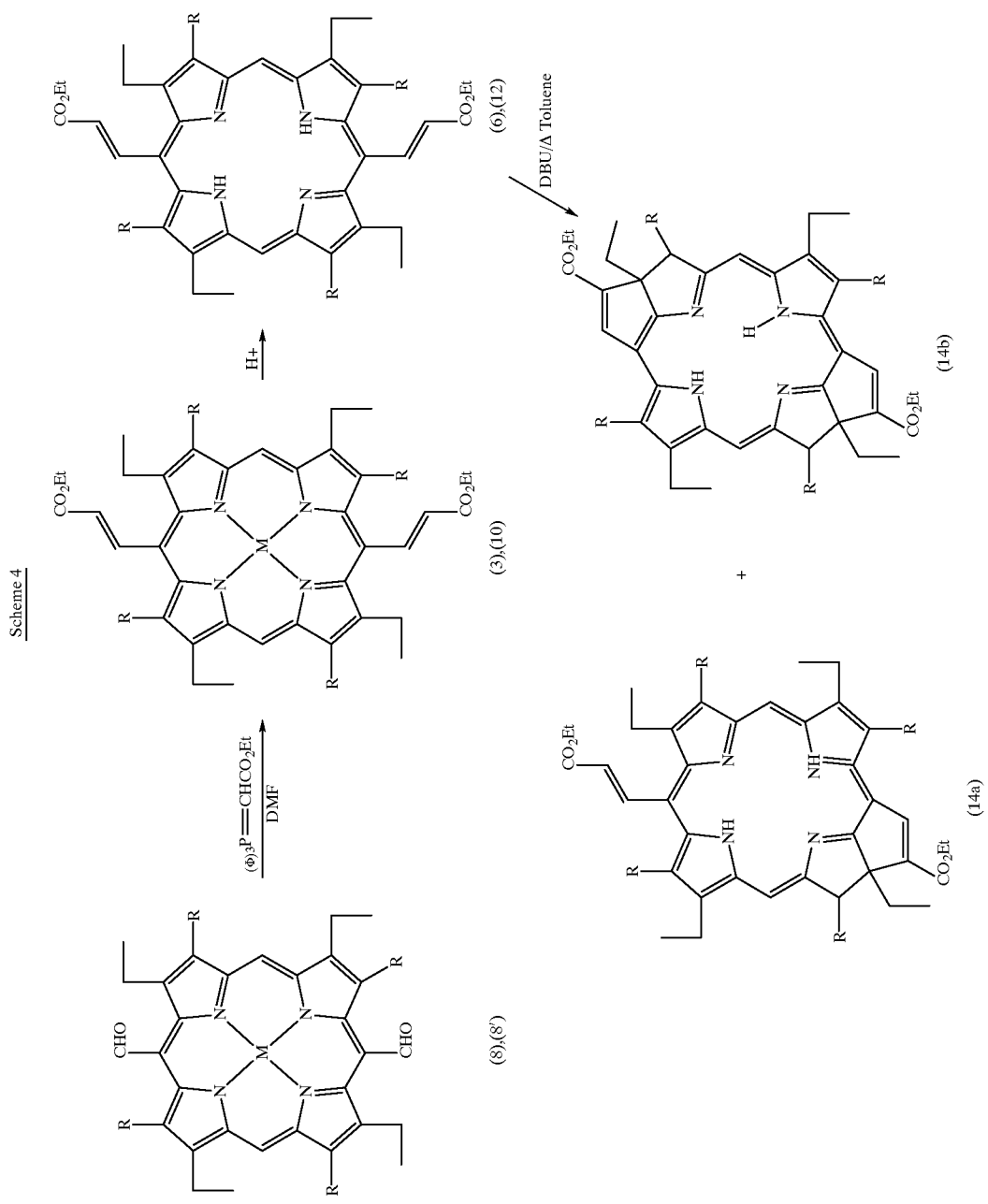

Clearly, the scope of the invention is not limited to the examples shown. A large number of porphyrins are known in the literature (for example see "Porphyrins and Metalloporphyrins" ed. K. Smith, Elsevier, 1975, N.Y. and "The Porphyrins", Ed D. Dolphin, Vol I–V, Academic Press, 1978–7) which contain various and ranging substituents on the β-pyrrole positions or meso-positions of the porphyrin ring, either symmetrically or asymmetrically substituted on the ring. Examples of such functionality may be functional groups having a molecular weight less than or equal to about 100,000 daltons can be (1) hydrogen; (2) halogen, such as fluoro, chloro, iodo and bromo; (3) lower alkyl, such as methyl, ethyl, n-propyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salts, such as —$CH_2COOH$, —$CH_2COO$—$Na^+$, —$CH_2CH_2COOH$, —$CH_2CH_2COONa$, —$CH_2CH_2CH(Br)COOH$, —$CH_2CH_2CH(CH_3)COOH$, —$CH_2CH(Br)COOH$, —$CH_2CH(CH_3)COOH$, —$CH(Cl)$—$CH_2$—$CH(CH_3)$—$COOH$, —$CH_2$—$CH_2$—$C(CH_3)_2$—$COOH$, —$CH_2$—$CH_2$—$C(CH_3)_2$—$COO^-K^+$, —$CH_2$—$CH_2$-$CH_2$—$CH_2$—$COOH$, $C(CH_3)_3$—$COOH$, $CH(Cl)_2$—$COOH$ and the like; (7) carboxylic acid esters, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_2CH_3$, —$CH_2CH(CH_3)_2COOCH_2CH_3$, and the like; (8) sulfonic acid or acid salts, for example, group I and group II salts, ammonium salts, and organic cation salts such as alkyl and quaternary ammonium salts; (9) sulfonylamides such as substituted and unsubstituted benzene sulfonamides; (10) sulfonic acid esters, such as methyl sulfonate, ethyl sulfonate, cyclohexyl sulfonate and the like; (11) amino, such as unsubstituted primary amino, methylamino, ethylamino, n-propylamino, isopropylamino, 5-butylamino, sec-butylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino) heptyl, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (12) cyano; (13) nitro; or (14) a biologically active group; or (15) any other substituent that increases the amphiphilic nature of the compounds of formulae IA, IB, IIIA, or IIIB.

The term "biologically active group" can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructo-furanose; (5) O-acyl derivatives such as penta-O-acetyl-α-glucose; (6) O-methyl derivatives such as methyl α-glucoside, methyl β-glucoside, methyl α-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, δ-gluconolactone, δ-glucuronolactone, ascorbic acid, and dehydroascorbic acid; (10) phosphoric acid esters such as α-glucose 1-phosphoric acid, α-glucose 6-phosphoric acid, α-fructose 1,6-diphosphoric acid, and α-fructose 6-phosphoric acid; (11) deoxy sugars such as 2-deoxyribose, rhammose (deoxy-mannose), and fructose (6-deoxygalactose); (12) amino sugars such as glucosamine and galactosamine; muramic acid and neurarninic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as α-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; (4) neurotransmitters, such as acetylcholine, serotonin, dopamine, and the like; and (5) antibodies. Any analog of these substances that also succeeds in binding to a biological receptor is also included.

Particularly useful examples of substituents tending to increase the amphiphilic nature of the compounds of formulae IA, IB, IIIA, and IIIB include: (1) long chain alcohols, for example, —$C_{12}H_{24}$—OH where —$C_{12}H_{24}$ is hydrophobic; (2) fatty acids and their salts, such as the sodium salt of the long-chain fatty acid oleic acid; (3) phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; (4) sphingolipids, such as sphingomyelin; and (5) glycolipids, such as glycosyldiacylglycerols, cerebrosides,sulfate esters of cerebrosides or gangliosides. The scope of the invention is limited only in the fact that at least two acrylate groups must be present on the molecule to effect the base catalyzed transformation for meso-diacrylate porphyrin to bacteriopurpin as shown by Schemes 1 and 2.

A wide number of purpurins have been made from porphyrins bearing different functionality from meso-acrylate groups. These include but are not limited to; —CHCH-CHO, CHCHCN, CHCHC(NH)(NH$_2$), CHCHCO$_2$R (where R can be alkyl, aryl or any other functionality of interest), CHCHCONHR, CHCHCONR$_1$R$_2$, (or any other amide of interest), or CHCHCH$_2$OR, for example. Such groups will be called meso-vinylic substituents and porphyrins bearing two of these groups will be called meso-divinylic substituted porphyrins. It may be envisaged that such meso-di-vinylic substituted porphyrins may be synthesized and cyclized according to the chemistry outlined. Indeed, it may also be envisaged that porphyrins bearing different meso-divinylic substituents may be synthesized and likewise cyclized to produce bacteriopurpurins bearing these substituents. Such structures may be represented by the following structures:

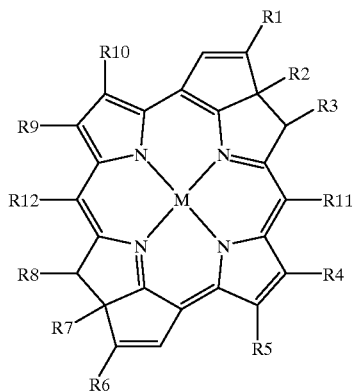

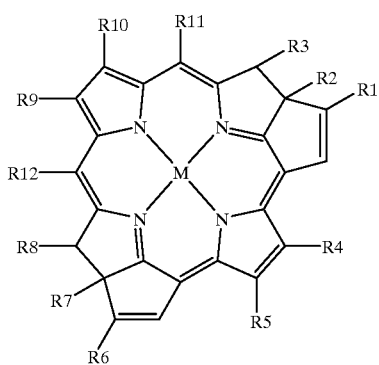

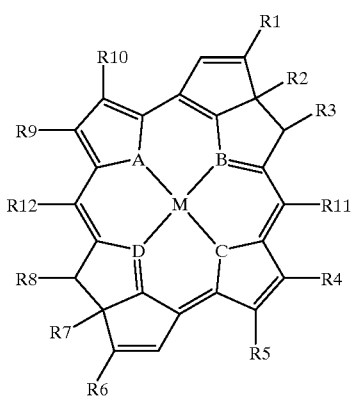

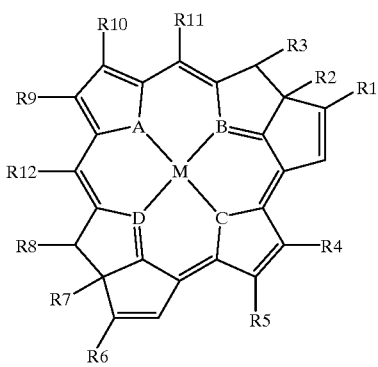

where A, B, C, D may be N, S, O, Se, Te, P or combinations thereof. Likewise there exist derivatives of porphyrins called azoporphyrins, in which one or more of the meso-carbon atoms has been replaced by nitrogen. Such molecules are well characterized in the literature (for instance in "The Porphyrins", Ed. D. Dolphin, Vol. I–V, Academic Press, 1978–1979) and have different spectroscopic characteristics from those of the porphyrins. Such azoporphyrins are also well known to bind metals and as such may be derivitized with meso-divinylic substituents. Such molecules may then be cyclized by the chemistry outlined to give bacteriopurpurins of the following structures:

Alternatively, there exists derivatives of porphyrins that have heteroatoms besides nitrogen in the central cavity of the porphyrinoid ring structure. Examples of such atoms include; S, O, Se, Te, P. Such molecules are known to bind metals and as such may be derivitized with meso-divinylic substituents. Such molecules may then be cyclized by the chemistry outlined to give bacteriopurpurins of the following structures:

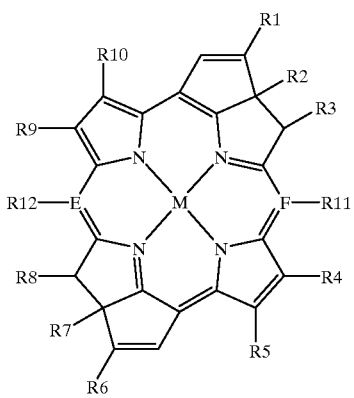

-continued

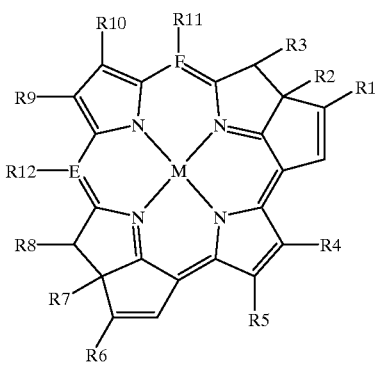

where E and F may be C or N or combinations thereof. Likewise it is possible to envisage porphyrins bearing nitrogens at the meso-positions and heteroatoms other than or including nitrogen in the central ring core. Such molecules may be derivitized with meso-divinylic substituents and may then be cyclized by the chemistry outlined to give bacteriopurpurins of the following structures:

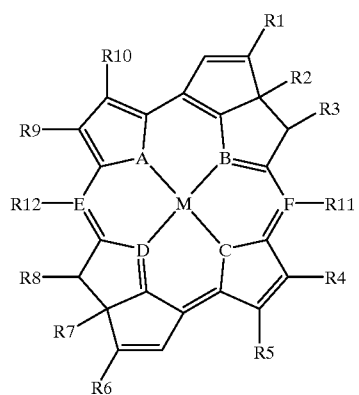

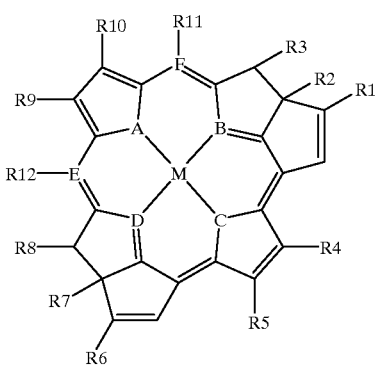

All such peripheral and ring functionality changes would be expected to produce molecules that have widely different spectrocopic properties, which may have useful application to various disease indications as photosensitizers in photodynamic therapy or as photodiagnostic agents.

It is well established that the double bond on the isocyclic ring of purpurins may be hydrogenated by hydrogenation catalysts such as Pd/C, Pt/C or Ni/C. Other hydrogenation catalysts include rhodium, ruthenium and iridium metals or in conjunction within elements and compounds such as carbon and $Al_2O_3$. Hydrogenation of the double bond on the isocyclic ring yields a single bond (See e.g., Morgan, A. R., et al. J. Org. Chem., 1986, 51, 1347). In bacteriopurpurins it is also possible to hydrogenate the isocyclic ring double bonds by similar hydrogenation catalysts and derivatives thereof may be synthesized by hydrogenation of bacteriopurpurins as described herein. Such modification to the isocylic ring structures would be expected to produce molecules that have widely different spectrocopic properties, which may have useful application to various disease indications as photosensitizers in photodynamic therapy or as photodiagnostic agents.

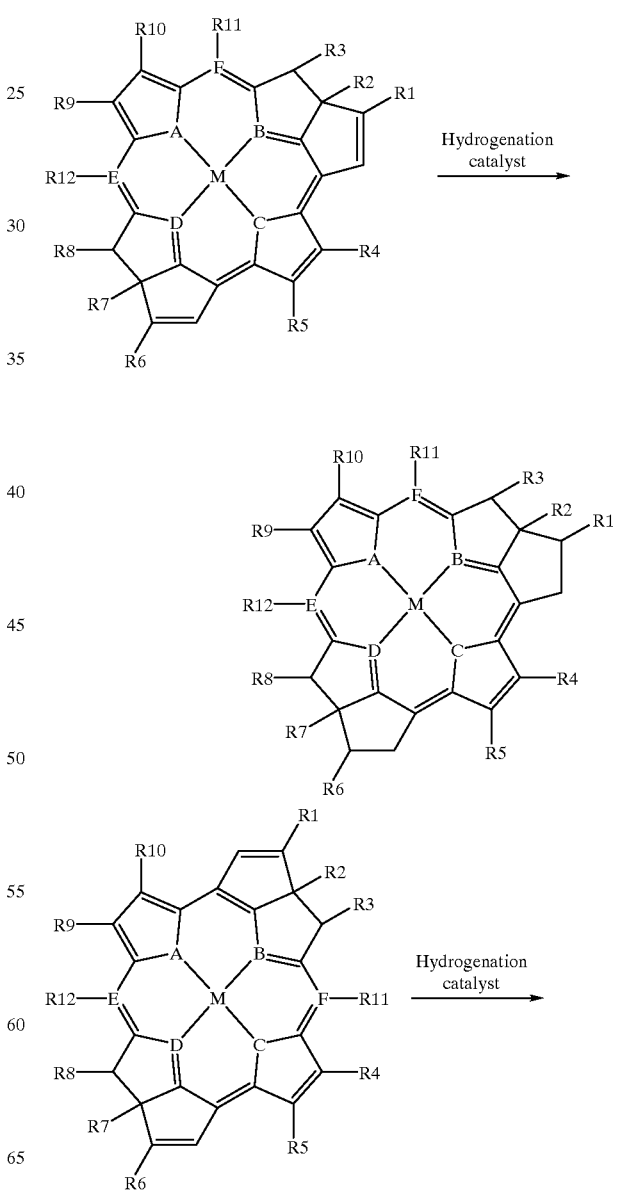

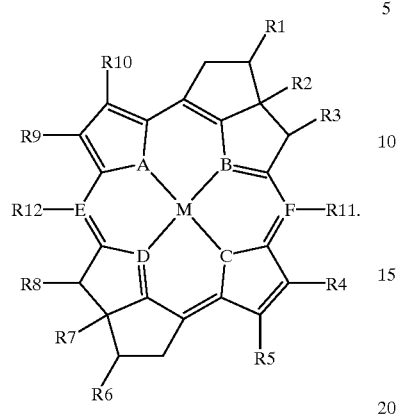
Selective hydrogenation and purification can produce:
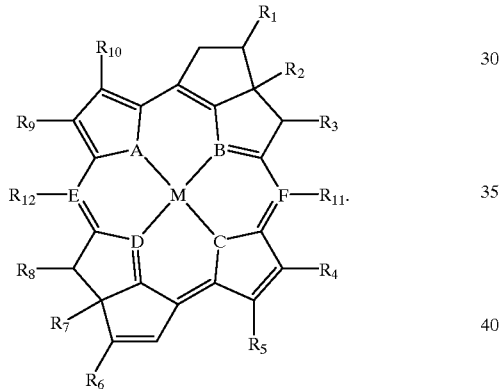
The present invention also provides for the following photodynamic compounds:
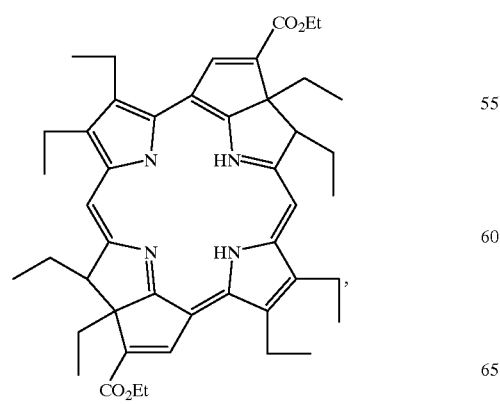
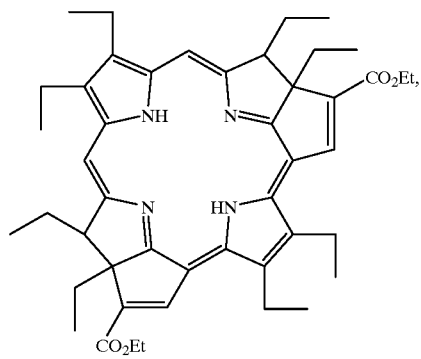
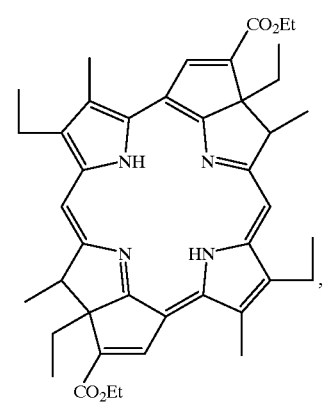
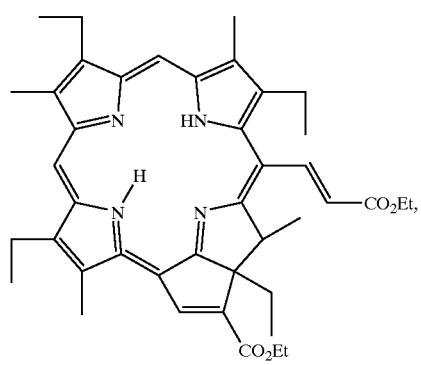

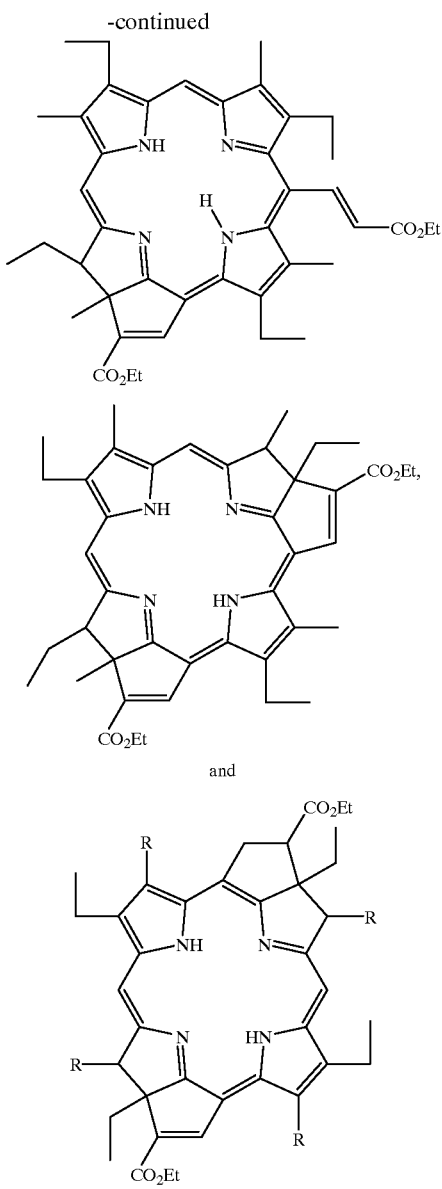

wherein R is Me or Et.

The compounds of the present invention, or their pharmaceutically acceptable salts, solvates, prodrugs, or metabolites, can be administered to the host in a variety of forms adapted to the chosen route of administration, i.e., orally, intravenously, intramuscularly or subcutaneously.

The active compound may be orally administered, for example, with an inert diluent or with an assimilable edible carrier, or it may be enclosed in hard or soft shell gelatin capsule, or it may be compressed into tablets, or it may be incorporated directly with food. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of the administered product. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potatostarch, alginic acid and the like; a lubricant such as magnesium stearate; a sweetening agent such as sucrose, lactose or saccharin; or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions, dispersions, or liposomal or emulsion formulations. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required additional ingredients from those enumerated above. In the case of sterile powders for the preparation of sterile injectable solutions, the preferred methods of preparation are vacuum drying and the freeze-drying technique, which yield a powder of the active ingredient plus any additional desired ingredient from previously sterile-filtered solutions thereof.

The present new compounds may also be applied directly to tumors in the host whether internal or external, in topical compositions. Exemplary compositions include solutions of the new compounds in solvents, particularly aqueous solvents, most preferably water. Alternatively, for topical application particularly to skin tumors, the present new compounds may be dispersed in the usual cream or salve formulations commonly used for this purpose (such as liposomes, ointments, gels, hydrogels, and oils) or may be provided in the form of spray solutions or suspensions which may include a propellant usually employed in aerosol preparations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifications for the novel dosage unit forms of the invention are dictated by and directly dependent on (a) the unique characteristics of the active material and the particular therapeutic effect to be achieved, and (b) the limitations inherent in the art of compounding such an active material for the treatment of tumors in living subjects.

The following examples are given to highlight some preferred modes of synthesizing bacteriopurpurin molecules and are not intended to limit the scope of the invention.

EXAMPLES

In the following examples silica gel 60 (230–400 mesh) was used for column chromatography. Analytical thin layer chromatography was performed on Merck 60 F254 silica gel (precoated on aluminum). $^1$H spectra were recorded using a Unity Inova Varian 500 MHz spectrometer, chemical shifts of proton spectra are expressed in parts per million relative to the chloroform signal in deuterated chloroform (set at 7.24ppm). Electronic spectra were recorded on a Beckman DU 640 spectrophotometer. High resolution mass spectra were obtained on a VG 70SE double focussing mass spectrometer equipped with an oversize data system.

Example 1

Nickel 5, 10-bis-acrylate octaethylporphyrin (4) and Nickel 5, 15-bis-acrylate octaethylporphyrin (3)

Nickel acrylate octaethylporphyrin (5.0 g) was dissolved in dichloroethane (200 mL) and 10 g of Vilsmeier reagent was added. The solution was warmed at 65° C. for 2 hours after which no starting material remained. A saturated sodium acetate solution (100 mL) was added and the solution was heated at 65° C. for a further 3 hours with rapid stirring. The organic layer was collected and rotoevaporated to dryness. The solid was dissolved in dichloromethane (20 mL) and flash columned on silica using dichloromethane as solvent. The major green fraction was collected and evaporated to dryness. The next day the solid was dissolved in DMF (70 mL) and carbethoxymethylene triphenylphosphorane (10 g) was added. Argon was bubbled through the solution for 15 min and the solution was then heated at reflux under argon for 8 hours, after which no starting material remained. The DMF was removed by rotary evaporation and the solid was dissolved in dichloromethane (70 mL). The solution was chromatographed on silica using 40% hexane/dichloromethane as eluent, and the major red fraction collected. The solvent was removed by rotary evaporation. The red solid was dissolved in toluene (20 mL) and chromatographed on silica using toluene as eluent. Two major fractions were collected, each being crystallized from dichloromethane/ethanol. The first green fraction eluted was Nickel 5, 15 bis-acrylate octaethylporphyrin (3). Yield=3.0 g (54%).
$^1$HNMR: (CDCl$_3$) δ=1.29 (t, 6H, 2×CO$_2$CH$_2$CH$_3$), 1.59 (t, 12H, 4×CH$_2$CH$_3$), 1.65 (t, 12H, 4×CH$_2$CH$_3$), 3.67 (m, 16H, 8×CH$_2$), 4.257 (q, 4H, 2×CO$_2$CH$_2$), 5.22 (d, 2H, vinylicH), 9.17 (s, 2H, meso-H), 9.87 (d, 2H, vinylic-H) ppm.

The second green fraction was the Nickel 5, 10-bis-acrylate octaethylporphyrin. Yield=3.0 g.
$^1$HNMR: (CDCl$_3$) δ=1.29 (t, 6H, 2×CO$_2$CH$_2$CH$_3$), 1.52 (t, 6H, 2×CH$_2$CH$_3$), 1.61 (t, 6H, 2×CH$_2$CH$_3$), 1.64 (t, 6H, 2×CH$_2$CH$_3$), 1.7 (t, 6H, 2×CH$_2$CH$_3$), 3.68 (m, 16H, 8×CH$_2$), 4.26 (q, 4H, 2×CO$_2$CH$_2$), 5.18 (d, 2H, vinylic-H), 9.16 (s, 2H, meso-H), 9.87 (d, 2H, vinylic-H) ppm.

Example 2

5, 10-bis-acrylate octaethylporphyrin (5)

Nickel 5, 10-bis-acrylate octaethylporphyrin (2.0 g) was dissolved in dichloromethane 70 ml) and conc. sulfuric acid (10 mL) was added. The solution was stirred until the dichloromethane layer was colorless and then poured into a saturated bicarbonate solution (100 mL). The reaction flask was rinsed with dicloromethane/water solution and this was added to the reaction flask. The organic layer was collected and reduced in volume to ~25 mL. The organic layer was passed over a pad of silica gel using 2% acetone/dichloromethane as eluent and the major green fraction collected. The solvent was removed by rotary evaporation and the solid residue redissolved in dichloromethane (20 mL). Methanol ((30 mL) was added and the dichloromethane removed by rotary evaporation. The precipitated porphyrin was collected by filtration, washed with methanol and pumped to dryness. Yield=1.7 g of 5, 10-bis-acrylate octaethylporphyrin (5). Spectral properties were identical to those described in the literature (Morgan, A. R., Skalkos, D., Garbo, G. M., Keck, R. W., Selmen, S. H., Journal of Medicinal chemistry, 1991, 43, 2126–2133.

Example 3

5, 15-bis-acrylate octaethylporphyrin (6)

Nickel 5, 15-bis-acrylate octaethylporphyrin (1.0 g) was dissolved in dichloromethane (30 ml) and conc. sulfuric acid (7 mL) was added. The solution was stirred until the dichloromethane layer was colorless and then poured into a saturated bicarbonate solution (100 mL). The reaction flask was rinsed with dichloromethane/water solution and this was added to the reaction flask. The organic layer was collected and reduced in volume to ~25 mL. The organic layer was passed over a pad of silica gel using 2% acetone/dichloromethane as eluent and the major green fraction collected. The solvent was removed by rotary evaporation and the solid residue redissolved in dichloromethane (20 mL). Methanol (30 mL) was added and the dichloromethane removed by rotary evaporation. The precipitated porphyrin was collected by filtration, washed with methanol and pumped to dryness. Yield=0.7 g of 5, 15-bis-acrylate octaethylporphyrin (6). Spectral properties were identical to those described in the literature (Morgan, A. R., Skalkos, D., Garbo, G. M., Keck, R. W., Selman, S. H., Journal of Medicinal Chemistry, 1991, 43, 2126–2133.

Example 4

5, 15-Octaethylbacteriopurpurin (14b, R=Et) and 15-meso-acrylate Octaethylpurpurin (14a, R=Et)

5, 15-bis-acrylate octaethylporphyrin (6) (60 mg) was dissolved in toluene (20 mL) and DBU (0.1 mL) was added. The solution was refluxed under argon for 5 hours after which the solvent was removed by rotary evaporation. The residue was dissolved in dichloromethane (10 mL) and columned on silica using dichloromethane as eluent. The major bright green fraction was collected and rotary evaporated to dryness. The solid was dissolved in dichloromethane (5 mL) and methanol (10 mL) was added. The dichloromethane was removed by slow rotary evaporation and the solid bacteriopurpurin collected by filtration. The solid was pumped dry under vacuum to give 46 mg (76%). $^1$HNMR shows the compound to be 5, 15-octaethylbacteriopurpurin (14b).
$^1$HNMR: (CDCl$_3$) δ=−0.16 (t, 6H, CH$_3$ of sp$^3$ ethyl's), 0.59 (s, 2H, NH), 1.54 (t, 6H), 2×CO$_2$CH$_2$CH$_3$), 1.63 (t, 6H, CH$_2$CH$_3$), 1.65 (t, 6H, CH$_2$CH$_3$), 1.699 (t, 6H, CH$_2$CH$_3$), 1.69 (m, 2H, CH of sp$^3$ ethyl's), 2.62 (m, 2H, CH of sp$^3$ ethyl's), 2.93 (m, 2H, CH of sp$^3$ ethyl's), 3.17 (m, 2H, CH of sp$^3$ ethyl), 3.5–3.9 (m, 10H, 4×CH$_2$ and 2×CH), 4.49 (oq, 4H, 2×CO$_2$CH$_2$), 8.40 (brs, 2H, meso-H), 9.22 (s, 2H, 2× isocyclic ring H) ppm. Accurate mass Cal: 730.44578 (exact), Found: 730.44625. UV/vis: (CH$_2$Cl$_2$) λ$_{max}$ (nm) 365, 416, 499, 556, 593, 767, 846.

A second polar minor green/brown band was eluted from the column using 2% acetone/dichloromethane. The solvent was removed by rotary evaporation. Yield=5 mg. $^1$HNMR showed the compound to be 15-meso-acrylate octaethylpurpurin (14a).
$^1$HNMR: (CDCl$_3$) δ —0.6 (brs, 1H, NH), −0.21 (s, 3H, CH$_3$ of sp$^3$ methyl), 0.05 (brs, 1H, NH), 1.404 (t, 3H, CO$_2$CH$_2$CH$_3$), 1.45 (t, 3H, CO$_2$CH$_2$CH$_3$), 1.54 (t, 3H, CH$_3$), 1.56 (t, 3H, CH$_3$), 1.62 (t, 3H, CH$_3$), 1.64 (m, 2H, CH of sp$^3$ ethyl), 1.65 (t, 3H, CH$_3$), 1.68 (t, 3H, CH$_3$), 2.72 (m, 2H, CH of sp$^3$ ethyl), 3.07 (m, 2H, CH of sp$^3$ ethyl), 3.07 (m, 2H, CH of sp$^3$ ethyl), 3.24 (s, 6H, CH$_3$), 3.41 (s, 3H, CH$_3$), 3.72 (q, 2H, CH$_2$CH$_3$), 3.5–4.0 (om, 13H, 6×CH$_2$ and C18-H), 4.41 (q, 2H, CO$_2$CH$_2$CH$_3$), 4.51 (q, 2H, CO$_2$CH$_2$CH$_3$), 6.12 (d, 1H, vinylic-H), 8.61 (s,1 H, meso-H), 9.28 (s, 1H, isocyclic ring H*), 9.40 (s, 1H, meso-H*), 9.98 (d, 1H, vinylic-H) ppm.
* assignments may be interchanged as no CH correlation experiments were performed.

Example 5

5, 10-Octaethylbacteriopurpurin (13b, R=Et) and 10-meso-acrylate octaethylpurpurin (13a, R=Et)

5, 10-bis-acrylate octaethylporphyrin (5) (200 mg) was dissolved in toluene (30 mL) and DBU (0.1 mL) was added. The solution was refluxed under argon for 24 hours after which the solvent was removed by rotary evaporation. The residue was dissolved in dichloromethane (10 mL) and columned on silica using dichloromethane as eluent. Two major fractions were collected and rotary evaporated to dryness. The first bright green fraction corresponded to the desired bacteriopurpurin which was not able to be induced to crystallize. Yield=100 mg (50%). Proton NMR showed the compound to be a 50:50 mixture of geometric cyclization isomers of 5, 10-octaethylbacteriopurpurin (13b).
$^1$HNMR: (CDCl$_3$) δ=−0.29 (s, 1H, NH), −0.21 and −0.13* (2×t, 6H, CH$_3$ of sp$^3$ ethyl's), 0.03 (s, 1H, NH), 1.53 (t, 6H, 2×CO$_2$CH$_2$CH$_3$), 1.58–1.72 (ot, 18H, CH$_2$CH$_3$), 1.76 (m, 2H, CH of sp$^3$ ethyl's), 2.61 (m, 2H, CH of sp$^3$ ethyl's), 2.92 (m, 2H, CH of sp$^3$ ethyl's), 3.16 m, 2H, CH of sp$^3$ ethyl), 3.5–3.9 (m, 10H, 4×CH$_2$ and 2×CH), 4.48 and 4.49 (oq, 4H, CO$_2$CH$_2$), 8.41 and 8.44*(2×brs, 2H, meso-H), 9.195 and 9.197 (2×s, 2H, 2×isocyclic ring H) ppm. UV/vis: (CH$_2$Cl$_2$) λ$_{max}$ (nm) 370, 434, 563, 598, 696, 796, 863.

The second green fraction was the 10-meso-acrylate octaethylpurpurin (13a) which was crystallized from dichloromethane/methanol, filtered and pumped dry. Yield= 90 mg (45%).
$^1$HNMR: (CDCl$_3$) δ −0.40 (t, 3H, CH$_3$ of sp$^3$ methyl), −0.25 (s, 1H, NH), 0.49 (s, 1H, NH), 1.33 (t, 6H, 2×CO$_2$CH$_2$CH$_3$), 1.48 (t, 3H, CH$_3$), 1.53 (t, 3H, CH$_3$), 160 (t, 3H, CH$_3$), 1.61–1.8 (ot,m 13H, 4×CH$_3$ and CH of sp$^3$ ethyl), 2.95 (m, 1H, CH of sp$^3$ ethyl), 3.15 (m, 2H, 2×CH of sp$^3$ ethyl), 3.6–3.9 (m, 13H, CH and 6×CH$_2$), 4.30 (m, 2H, CO$_2$CH$_2$CH$_3$), 4.50 (m, 2H, CO$_2$CH$_2$CH$_3$), 5.52 (d, 1H, vinylic-H), 9.24 (s, 1H, meso-H*), 9.29 (s, 1H, isocyclic ring H*), 9.39 (s, 1H, meso-H*), 9.48 (d, 1H, vinylic-H) ppm.
(* No CH correlation experiments were performed to definitively assign peaks) UV/vis: (CH$_2$Cl$_2$) λ$_{max}$ (nm) 429, 505, 532, 570, 643, 700.

Example 6

Nickel 5, 15-bis-acrylate etioporphyrin I (10)

Nickel 5, 15-bis-formyl etioporphyrin I (8) (12.0 g) and carbethoxymethylene triphenylphosphorane (28 g) was dissolved in DMF (100 mL) and argon was bubbled through the solution for 15 min. The solution was heated at reflux under argon for 8 hours after which no starting material remained. The DMF was removed by rotary evaporation and the solid dissolved in dichloromethane (200 mL). MeOH (100 mL) was added and the dichloromethane removed by rotary evaporation. The precipitated solid was collected by filtration and dried. The solid was redissolved in hexane/dichloromethane (500 mL) and the solution chromatographed on silica (500 g) using 40% Hexane/dichloromethane as eluent, and a minor fraction collected and discarded. The column was then eluted with 25% hexane/dichloromethane and the major green fraction collected and rotoevaporated to dryness. The solid was redissolved in dichloromethane (150 mL) and methanol (150 mL) added. The dichloromethane was removed by rotary evaporation and the precipitated solid collected by filtration and vacuum dried. Yield=9.0 g (85%) of Ni 5, 15-bis acrylate etioporphyrin I (10).
$^1$HNMR: (CDCl$_3$) δ=1.30 (t, 6H, 2×CO$_2$CH$_2$CH$_3$), 1.57 (t, 12H, 4×CH$_2$CH$_3$), 1.60 (t, 12H, 4×CH$_2$CH$_3$), 3.19 (s, 6H, 2×CH$_3$), 3.23 (s, 6H, 2×CH$_3$), 3.65 (q, 4H, 2×CH$_3$), 3.18 (q, 4H, 2×CH$_2$), 4.27 (q, 4H, 2×CO$_2$CH$_2$), 5.25 (d, 2H, vinylic-H), 9.19 (s, 2H, meso-H), 9.84 (d, 2H, vinylic-H) ppm. FAB mass Cal: 730 (M+), Found: 730 (M+). UV/vis: (CH$_2$Cl$_2$) λ$_{max}$ (nm) 423, 590.

Example 7

Nickel 5, 10-bis-acrylate etioporphyrin I (9)

Nickel 5, 10-bis-formyl etioporphyrin I (7) (12.0 g) and carbethoxymethylene triphenylphosphorane (28 g) was dissolved in DMF (100 mL) and argon was bubbled through the solution for 15 min. The solution was heated at reflux under argon for 8 hours after which no starting material remained. The DMF was removed by rotary evaporation and the solid dissolved in dichloromethane (200 mL). EtOH (100 mL) was added and the dichloromethane removed by rotary evaporation. The precipitated solid was collected by filtration and dried. The solid was redissolved in hexane/dichloromethane (200 mL) and the solution chromatographed on silica (500 g) using 25% Hexane/dichloromethane as eluent, and a minor fraction collected and discarded prior to the collection of the main band. The major green fraction was collected and rotoevaporated to dryness. The solid was redissolved in dichloromethane (150 mL) and EtOH (100 mL) added. The dichloromethane was removed by rotary evaporation and the precipitated solid collected by filtration and vacuum dried. Yield=11.5 g of Ni 5, 10-bis-acrylate etioporphyrin I (9).

$^1$HNMR: (CDCl$_3$) δ=1.29 (t, 3H, CO$_2$CH$_2$CH$_3$), 1.30 (t, 3H, CH$_2$CH$_3$), 1.57 (t, 3H, CH$_2$CH$_3$), 1.58 (t, 3H, CH$_2$CH$_3$), 1.63 (t, 3H, CH$_2$CH$_3$), 3.13 (s, 3H, CH$_3$), 3.14 (s, 3H, CH$_3$), 3.21 (s, 3H, CH$_3$), 3.24 (s, 3H, CH$_3$), 3.58–3.72 (m, 8H, 4×CH$_2$), 4.255 (q, 2H, CO$_2$CH$_2$), 4.27 (q, 2H, CO$_2$CH$_2$), 5.21 (d, 1H, vinylic-H), 5.24 (d, 1H, vinylic-H), 9.15 (s, 1H, meso-H), 9.16 (s, 1H, meso-H), 9.77 (d, 1H, vinylic-H), 9.83 (d, 1H, vinylic-H) ppm. Accurate mass calculated 730.3029, Found: 730.3030. UV/vis: (CH$_2$Cl$_2$) λ$_{max}$ (nm) 425, 580.

Example 8

5, 10-bis-acrylate etioporphyrin (11)

Nickel 5, 10-bis-acrylate etioporphyrin I (9) (1.0 g) was dissolved in dichloromethane (50 mL) and concentrated sulfuric acid (10 mL) was added. The solution was stirred until the dichloromethane layer was colorless and then poured into a saturated sodium bicarbonate solution (100 mL). The reaction flask was rinsed with dichloromethane/water and this was added into the bicarbonate solution. The organic layer was collected and reduced in volume to ~20 mL. The organic solution was passed over a column of silica using 2% acetone dichloromethane as eluent and the major green fraction collected. The solvent was removed by rotary evaporation and the solid redissolved in dichloromethane (20 mL). Methanol (30 mL) was added and the dichloromethane was removed by rotary evaporation. The precipitated porphyrin was collected by filtration, washed with methanol and pumped to dryness. Yield=0.85 g of 5,1 0-bis-acrylate etioporphyrin (11).

$^1$HNMR: (CDCl$_3$) δ=–2.38 (brs, 2H, NH), 1.37 (t, 3H, CH$_2$CH$_3$), 1.47(t, 3H, CO$_2$CH$_2$CH$_3$), 1.48 (t, 3H, CO$_2$CH$_2$CH$_3$), 1.69 (t, 3H, CH$_3$), 1.72 (t, 3H, CH$_3$), 1.77 (t, 3H, CH$_3$), 2.88(s, 3H, CH$_3$), 3.31 (q, 2H, CH$_2$), 3.39 (s, 6H, 2×CH$_3$), 3.45 (s, 3H, CH$_3$), 3.89 (m, 6H, 3×CH$_2$), 4.47 (q, 4H, 2×CO$_2$CH$_2$), 6.24 (d, 1H, vinylicH), 6.35 (d, 1H, vinylic-H), 9.61 (s, 1H, meso-H), 9.62 (s, 1H, meso-H), 10.15 (d, 2H, vinylic-H), 10.20 (d, 2H, vinylic-H)ppm. Accurate mass calculated 675.391 (M+H$^+$), Found: 675.3907. UV/vis: (CH$_2$Cl$_2$) λ$_{max}$ (nm) 430, 592, 522.

Example 9

5, 15-bis-acrylate etioporphyrin (12)

Nickel 5, 15-bis-acrylate etioporphyrin I (10) (0.2 g) was dissolved in dichloromethane (50 mL) and concentrated sulfuric acid (5 mL) was added. The solution was stirred until the dichloromethane layer was colorless, then ice water (150 mL) was added. A solution of saturated sodium bicarbonate (50 mL) was added carefully to the solution and the organic layer separated and washed with water (100 mL). The organic layer was collected and dried over sodium sulfate, filtered and evaporated to dryness. The solid was dissolved in dichloromethane (20 mL) and methanol (10 mL) added. The dichloromethane was removed by rotary evaporation and the precipitated pink flocculate collected by filtration, washed with ethanol and pumped to dryness. Yield=170 mg of 5, 15-bis-acrylate etioporphyrin (12).

$^1$HNMR: (CDCl$_3$) δ=–2.38 (brs, 1H, NH), 1.44 (t, 6H, 2×CO$_2$CH$_2$CH$_3$), 1.62 (t, 6H, 2×CH$_2$CH$_3$), 1.76 (t, 6H, 2×CH$_2$CH$_3$), 3.32 (s, 6H, 2×CH$_3$), 3.56 (s, 6H, 2×CH$_3$), 3.87 (q, 4H, 2×CH$_2$), 3.97 (q, 4H, 2×CH$_2$), 4.45 (q, 4H, 2×CO$_2$CH$_2$), 6.20 (d, 2H, vinylic-H), 10.05 (s, 2H, meso-H), 10.18 (d, 2H, vinylic-H) ppm. Accurate mass calculated 674.3832, Found: 674.3838. UV/vis: (CH$_2$Cl$_2$) λ$_{max}$ (nm) 414, 511, 548, 579, 634.

Example 10

5, 15-Etiobacteriopurpurin (14b, R=Me)

5, 15-bis-acrylate etioporphyrin (12) (200 mg) was dissolved in toluene (20 mL) and DBU (0.1 mL) was added. The solution was refluxed under argon for 5 hours after which the solvent was removed by rotary evaporation. The residue was dissolved in dichloromethane (10 mL) and columned on silica using dichloromethane as eluent. The major bright green fraction was collected and rotary evaporated to dryness. The solid was dissolved in dichloromethane (5 mL) and methanol (10 mL) was added. The dichloromethane was removed by slow rotary evaporation and the solid bacteriopurpurin collected by filtration. The solid was pumped dry under vacuum to give 175 mg (88%) of a compound shown by $^1$HNMR to be 5, 15-etiobacteriopurpurin (14b).

$^1$HNMR: (CDCl$_3$) δ=–0.079 (t, 6H, CH$_3$ of sp$^3$ ethyl's), 0.61 (s, 2H, NH), 1.54 (t, 6H, 2×CO$_2$CH$_2$CH$_3$), 1.57 (t, 6H, CH$_2$CH$_3$), 1.65 (m, 2H, 2×CH of sp$^3$ ethyl's), 2.35 (d, 3H, CH$_3$), 2.57 (m, 2H, 2×CH of sp$^3$ ethyl's), 3.33 (s, 3H, ring CH$_3$), 3.58 (m, 4H, 2×CH$_2$), 4.20 (q, 2H, CH), 4.49 (q, 4H, 2×CO$_2$CH$_2$), 8.19 (s, 2H, meso-H), 9.29 (s, 2H, 2×isocyclic ring H) ppm. Accurate mass Cal: 674.3832 (exact), Found: 674.3817. UV/vis:(CH$_2$Cl$_2$) λ$_{max}$ (nm) 364, 415, 499, 558, 592, 768, 843.

Example 11

5, 10-Etiobacteriopurpurin (13b, R=Me) and 10-meso-Acrylate etiopurpurin (13a, R=Me)

5, 10-bis-acrylate etioporphyrin (11) (200 mg) was dissolved in toluene (20 mL) and DBU (0.1 mL) was added. The solution was refluxed under argon for 24 hours after which the solvent was removed by rotary evaporation. The residue was dissolved in dichloromethane (10 mL) and columned on silica using dichloromethane as eluent. Two fractions were collected, the first being a bright green fraction, etiobacteriopurpurin and the major fraction being 10-meso-acrylate etiopurpurin (13a). The two fractions were separately rotoevaporated to dryness. The bacteriopurpurin fraction could not be induced to crystallize. Yield=25 mg (12%). The major purpurin product was dissolved in dichlo romethane (10 mL) and methanol (10 mL) was added. The dichloromethane was removed by slow rotary evaporation and the precipitated purpurin collected by filtration. The solid was pumped dry under vacuum to give 155 mg (76%).

$^1$HNMR (13b, R=Me): (CDCl$_3$) δ==0.107 (t, 3H, CH$_3$ of sp$^3$ ethyl's), −0.06*(t, 3H, CH$_3$ of sp3 ethyl's), 0.04 (s, 2H, NH), 1.35 (s, 3H, CH$_3$), 1.48–1.75 (ot, 15H, 2×CO$_2$CH$_2$CH$_3$, 3×CH$_3$), 2.58 (m, 1H, CH of sp$^3$ ethyl's), 2.92 (m, 1H, CH of sp3 ethyl's), 2.35 (d, 3H, CH$_3$), 2.36*(d, 3H, CH$_3$), 2.57 (m, 2H, 2×CH of sp3 ethyl's), 3.13*(s, 3H, ring CH$_3$), 3.16 (s, 3H, ring CH$_3$), 3.34*(s, 3H, ring CH$_3$), 3.13*(s, 3H, ring CH$_3$), 3.38 (s, 3H, ring CH$_3$), 3.5–3.9 (m, 4H, 2×CH$_2$), 4.05 (q, 2H, CH), 4.49 (oq, 4H, 2×CO$_2$CH$_2$), 8.24 (s, 1H, meso-H), 8.27*(s, 1H, meso-H), 8.45 (s, 1H, meso-H) 8.48*(s, 1H, meso-H), 9.133* (s, 1H, isocyclic ring H), 9.139 (s, H, isocyclic ring H), 9.268*(s, H, isocyclic ring H), 9.276 (s, H, isocyclic ring H) ppm. Accurate mass Cal: 674.3832 (exact), Found: 674.3817. UV/vis: (CH$_2$CO$_2$) λ$_{max}$ (nm) 370, 407, 569, 596, 803, 861. 10-meso-Acrylate etiopurpurin (13a, R=Me)

$^1$HNMR: (CDCl$_3$) δ −0.381 (brs, 1H, NH), −0.32 (t, 3H, CH$_3$ of sp$^3$ ethyl), 0.33 (brs, 1H, NH), 1.35 (t, 3H, CO$_2$CH$_2$CH$_3$), 1.50 (m, 1H, CH of sp3 ethyl), 1.52 (t, 3H, CH$_3$), 1.54 (t, 3H, CH$_3$), 1.65 (t, 3H, CH$_3$), 1.67 (t, 3H, CH$_3$), 2.50 (d, 3H, CH3), 2.58 (m, 1H, CH of sp$^3$ ethyl), 3.23 (s, 6H, CH$_3$), 3.35 (s, 3H, CH$_3$), 3.45 (s, 3H, CH$_3$), 3.6–3.9 (om, 6H, 3×CH$_2$), 4.33 (q, 2H, CO$_2$CH$_2$CH$_3$), 4.495 (q, 2H, CO$_2$CH$_2$CH$_3$), 4.58 (q, 1H, C118-H), 5.59 (d, 1H, vinylic-H), 9.27 (s, 1H, meso-H), 9.42 (s, 2H, isocyclic ring H and meso-H), 9.53 (d, 1H, vinylic-H) ppm. UV/vis: (CH$_2$Cl$_2$) λ$_{max}$ (nm) 430, 503, 531, 570, 643, 701. Accurate mass Cal: 674.3832(exact), Found: 674.3831.

Example 12

5, 15-Bacterioetiochlorin 5, 15-Etiobacteriopurpurin (50 mg) was dissolved in tetrahydrofuran (15 mL) and Pd/C (200 mg) added. The solution was hydrogenated under a hydrogen atmosphere for 24 hrs. An aliquot of the solution, re-oxidized with air showed the absence of any starting material (844 nm) or of mono reduction (806 nm). The solution was filtered to remove the Pd/C catalyst and the solution stirred for 0.5 hrs in the presence of air. The solution was evaporated to dryness and the crude residue was dissolved in dichloromethane and methanol was added. The dichloromethane was removed by rotary evaporation and the precipitated bacteriochlorin was collected by filtration, washed with methanol, recrystalized from dichloromethane and methanol, filtered and dried. Yield=40 mg.

$^1$HNMR: (CDCl$_3$) δ 0.75 (brs, 2H, NH), −0.15 (t, 6H, CH$_3$ of sp$^3$ ethyl), 1.4–1.65 (ot, 15H 3×CH$_3$, 2×CO$_2$CH$_2$CH$_3$), 1.75 (m, 4H, CH of sp$^3$ ethyl), 2.15 (d, 6H, 2×CH3), 2.58 (m, 1H, CH of sp$^3$ ethyl), 3.22 (s, 6H, CH$_3$), 3.65 (om, 6H, 3×CH$_2$), 4.09 (dofd, 2H, 2xisocyclic ring H), 4.45 (om, 4H, 2×CO$_2$CH$_2$CH$_3$), 4.62 (dofd, 2H, 2× isocyclic ring H), 4.92 2xisocyclic ring H), 8.07 (s, 2H, meso-H)ppm. λ$_{max}$ (CH$_2$Cl$_2$); 761, 725, 696, 517, 487, 454, 385, 357 nm.

What is claimed is:

1. A compound of formulae IA or IB:

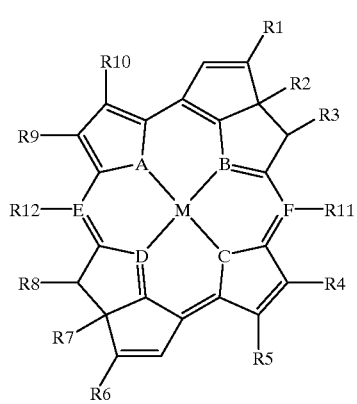

IA

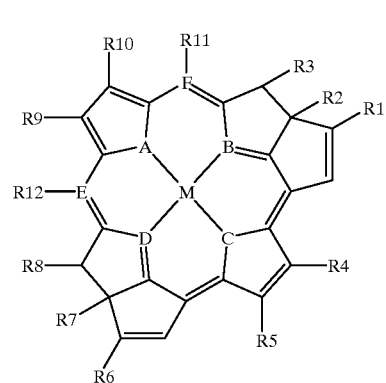

IB wherein:

R$_1$, R$_2$, R$_3$, R$_4$, R$_5$, R$_6$, R$_7$, R$_8$, R$_9$, R$_{10}$, R$_{11}$, and R$_{12}$ are independently selected from hydrogen, halogen atoms, unsubstituted or substituted alkyl, C$_3$–C$_6$ cycloalkyl, aryl, alkenyl, alkynyl, amides, esters, NR$_{13}$R$_{14}$, CN, OH, OR$_{13}$, CHO, (CH$_2$)$_n$OH, (CH$_2$)$_n$SH, (CH$_2$)$_n$O-alkoxy, (CH$_2$)$_n$SR$_{13}$, (CH$_2$)$_n$OR$_{13}$, (CH$_2$)$_n$CO$_2$R$_{13}$, (CH$_2$)$_n$CONHR$_{13}$, (CH$_2$)$_n$CON(R$_{13}$)(R$_{14}$), CO$_2$R$_{13}$, CONHR$_{13}$, CONR$_{13}$R$_{14}$, SR$_{13}$, SO$_3$H, SO$_3$R$_{13}$, SO$_2$N(R$_{13}$)(R$_{14}$), and SO$_2$N(R$_{13}$)(R$_{14}$)(R$_{15}$)$^+$X$^-$;

R$_{13}$, R$_{14}$, and R$_{15}$ are independently selected from hydrogen, a physiologically acceptable salt, unsubstituted or substituted C$_1$–C$_6$ alkyl, aryl, alkenyl, or alkynyl, and a functional group having a molecular weight less than or equal to 100,000 daltons;

n is an integer ranging from 1 to 4;

M is two hydrogens or a metal ion selected from Ag, Al, Ce, Co, Cr, Cu, Dy, Er, Eu, Fe, Gd, Hf, Ho, In, La, Lu, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr; and A, B, C and D are N, and E and F are C.

2. A compound of formulae IIA or IIB:

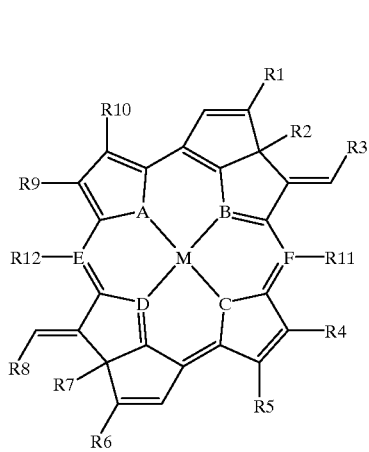

IIA

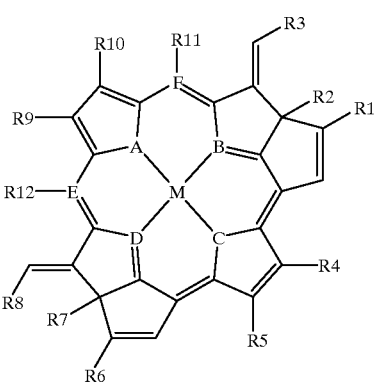

IIB wherein:

- $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, halogen atoms, unsubstituted or substituted alkyl, $C_3$–$C_6$ cycloalkyl, aryl, alkenyl, alkynyl, amides, esters, $NR_{13}R_{14}$, CN, OH, $OR_{13}$, CHO, $(CH_2)_nOH$, $(CH_2)_nSH$, $(CH_2)_nO$-alkoxy, $(CH_2)_nSR_{13}$, $(CH_2)_nOR_{13}$, $(CH_2)_nCO_2R_{13}$, $(CH_2)_nCONHR_{13}$, $(CH_2)_nCON(R_{13})(R_{14})$, $CO_2R_{13}$, $CONHR_{13}$, $CONR_{13}R_{14}$, $SR_{13}$, $SO_3H$, $SO_3R_{13}$, $SO_2NHR_{13}$, $SO_2N(R_{13})(R_{14})$, and $SO_2N(R_{13})(R_{14})(R_{15})^+X^-$;
- $R_{13}$, $R_{14}$, and $R_{15}$ are selected from hydrogen, a physiologically acceptable salt, unsubstituted or substituted $C_1$–$C_6$ alkyl, aryl, alkenyl, or alkynyl, and a functional group having a molecular weight less than or equal to 100,000 daltons;
- n is an integer ranging from 1 to 4;
- M is two hydrogens or a metal ion selected from Ag, Al, Ce, Co, Cr, Cu, Dy, Er, Eu, Fe, Gd, Hf, Ho, In, La, Lu, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr; and
- A, B, C and D are N, and E and F are C.

3. A compound of formulae IIIA or IIIB:

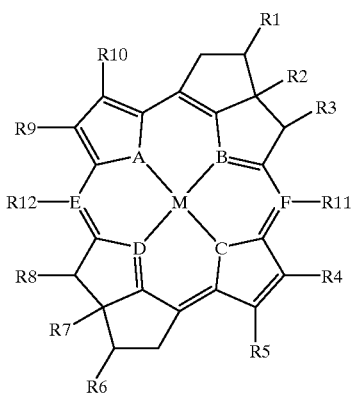

IIIA

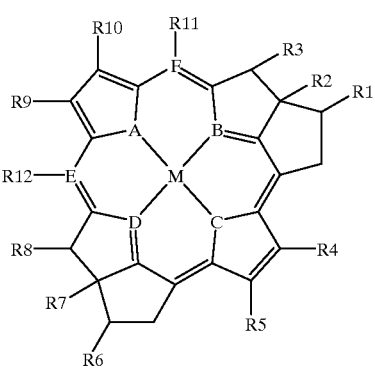

IIIB wherein:

- $R_1$, $R_2$, $R_3$, $R_4$, $R_5$, $R_6$, $R_7$, $R_8$, $R_9$, $R_{10}$, $R_{11}$, and $R_{12}$ are independently selected from hydrogen, halogen atoms, unsubstituted or substituted alkyl, $C_3$–$C_6$ cycloalkyl, aryl, alkenyl, alkynyl, amides, esters, $NR_{13}R_{14}$, CN, OH, $OR_{13}$, CHO, $(CH_2)_nOH$, $(CH_2)_nSH$, $(CH_2)_nO$-alkoxy, $(CH_2)_nSR_{13}$, $(CH_2)_nOR_{13}$, $(CH_2)_nCO_2R_{13}$, $(CH_2)_nCONHR_{13}$, $(CH_2)_nCON(R_{13})(R_{14})$, $CO_2R_{13}$, $CONHR_{13}$, $CONR_{13}R_{14}$, $SR_{13}$, $SO_3H$, $SO_3R_{13}$, $SO_2NHR_{13}$, $SO_2N(R_{13})(R_{14})$, and $SO_2N(R_{13})(R_{14})(R_{15})^+X^-$;
- $R_{13}$, $R_{14}$, and $R_{15}$ are independently selected from hydrogen, a physiologically acceptable salt, unsubstituted or substituted $C_1$–$C_6$ alkyl, aryl, alkenyl, or alkynyl, and a functional group having a molecular weight less than or equal to 100,000 daltons;
- n is an integer ranging from 1 to 4;
- M is two hydrogens or a metal ion selected from Ag, Al, Ce, Co, Cr, Cu, Dy, Er, Eu, Fe, Gd, Hf, Ho, In, La, Lu, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr; and
- A, B, C and D are N, and E and F are C.

4. A compound selected from the group consisting of
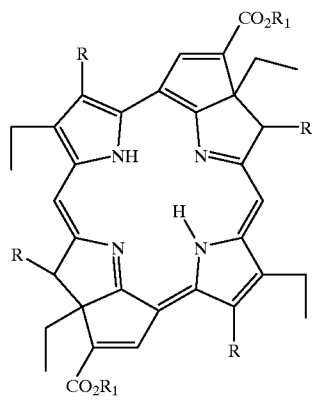
and
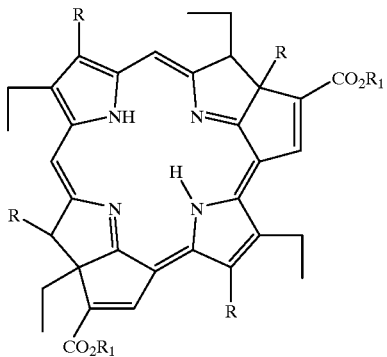
wherein R is methyl or ethyl and $R_1$ is alkyl or aryl.
5. The compound of claim 4 wherein $R_1$ is ethyl.
6. A compound selected from the group consisting of
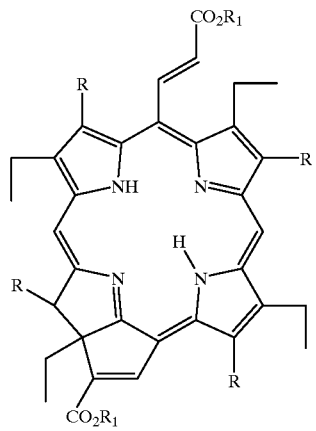
and
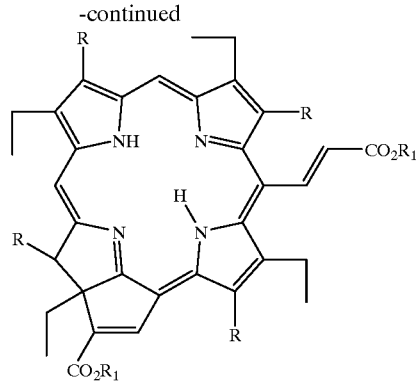
wherein R is methyl or ethyl and $R_1$ is alkyl or aryl.
7. The compound of claim 6 wherein $R_1$ is ethyl.
8. A compound selected from the group consisting of
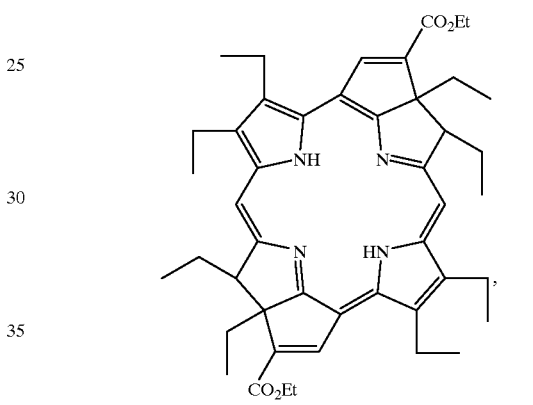
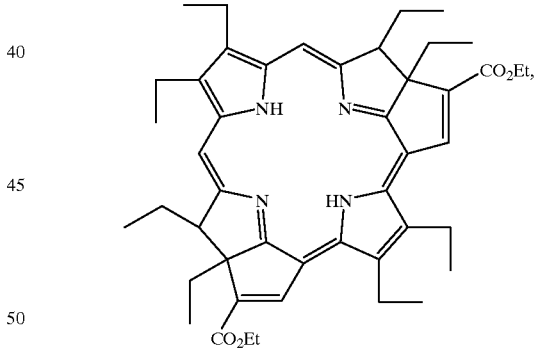
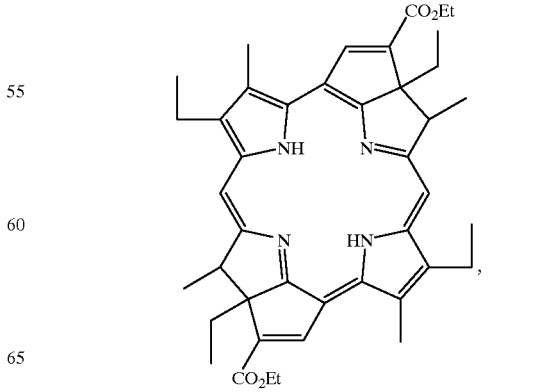

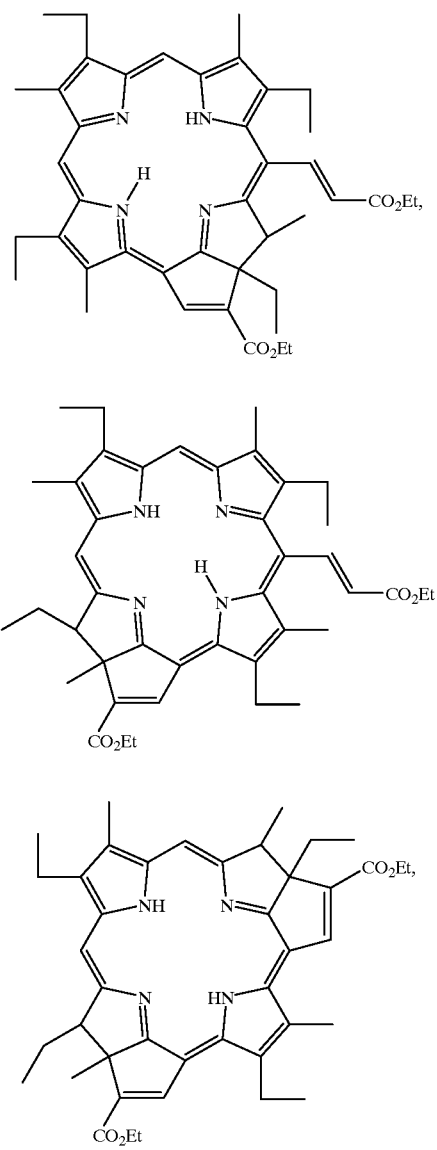
wherein R is Me or Et.
9. A compound selected from the group consisting of
wherein R is methyl or ethyl and $R_1$ is aryl or alkyl.
10. The compound of claim 9 wherein $R_1$ is ethyl.
11. A compound of formulae XVI or XVII:

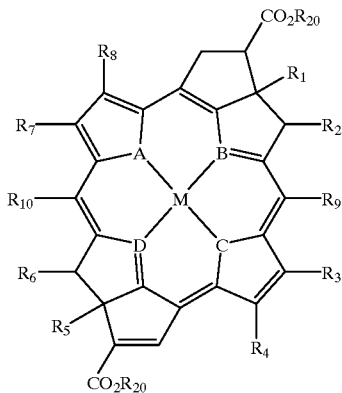

XVII wherein:
R$_1$, R$_2$, R$_3$, R$_4$, R$_5$, R$_6$, R$_7$, R$_8$, R$_9$, R$_{10}$, R$_{11}$, and R$_{12}$ are independently s from hydrogen, halogen atoms, unsubstituted or substituted alkyl, C$_3$–C$_6$ cycloalkyl, aryl, alkenyl, alkynyl, amides, esters, NR$_{13}$R$_{14}$, CN, OH, OR$_{13}$, CHO, (CH$_2$)$_n$OH, (CH$_2$)$_n$SH, (CH$_2$)$_n$O-alkoxy, (CH$_2$)$_n$SR$_{13}$, (CH$_2$)$_n$OR$_{13}$, (CH$_2$)$_n$CO$_2$R$_{13}$, (CH$_2$)$_n$CONHR$_{13}$, (CH$_2$)$_n$CON(R$_{13}$)(R$_{14}$), CO$_2$R$_{13}$, CONHR$_{13}$, CONR$_{13}$R$_{14}$, SR$_{13}$, SO$_3$H, SO$_3$R$_{13}$, SDO$_2$NHR$_{13}$, SO$_2$N(R$_{13}$)(R$_{14}$), and SO$_2$N(R$_{13}$)(R$_{14}$)(R$_{15}$)+X$^-$;

R$_{13}$, R$_{14}$, and R$_{15}$ are independently selected from hydrogen, a physiologically acceptable salt, unsubstituted or substituted C$_1$–C$_6$ alkyl, aryl, alkenyl, or alkynyl, and a functional group having a molecular weight less than or equal to 100,000 daltons;

n is an integer ranging from 1 to 4;

R$_{20}$ is an ubsubstituted or substituted C$_1$–C$_6$ alkyl;

M is two hydrogens or a metal ion selected from Ag, Al, Ce, Co, Cr, Cu, Dy, Er, Eu, Fe, Gd, Hf, Ho, In, La, Lu, Mn, Mo, Nd, Ni, Pb, Pd, Pr, Pt, Rh, Sb, Sc, Sm, Sn, Tb, Th, Ti, Tl, Tm, U, V, Y, Yb, Zn, and Zr; and A, B, C and D are N, and E and F are C.

12. A compound of formula XVIII

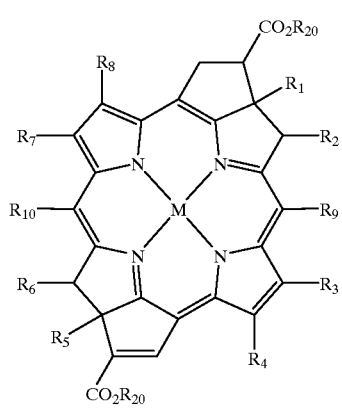

XVIII wherein R$_1$, R$_2$, R$_3$, R$_4$, R$_5$, R$_6$, R$_7$, R$_8$, R$_9$, and R$_{10}$ are independently selected from hydrogen, halogen atoms, unsubstituted or substituted alkyl, C$_3$–C$_6$ cycloalkyl, acetyl, aryl, alkenyl, alkynyl, amides, esters, NR$_{13}$R$_{14}$, CN, OH, OR$_{13}$, CHO, (CH$_2$)$_n$OH, (CH$_2$)$_n$SH, (CH$_2$)$_n$O-alkoxy, (CH$_2$)$_n$SR$_{13}$, (CH$_2$)$_n$OR$_{13}$, (CH$_2$)$_n$CO$_2$R$_{13}$, (CH$_2$)n (CH$_2$)$_n$CON(R$_{13}$)(R$_{14}$), CO$_2$R$_{13}$, CONHR$_{13}$, CONR$_{13}$R$_{14}$, SR$_{13}$, SO$_3$H, SO$_3$R$_{13}$, SO$_2$NHR$_{13}$, SO$_2$N(R$_{13}$)(R$_{14}$), and SO$_2$N(R$_{13}$)(R$_{14}$)(R$_{15}$)+X$^-$;

R$_{13}$, R$_{14}$, and R$_{15}$ are independently selected from hydrogen, a physiologically acceptable salt, unsubstituted or substituted C$_1$–C$_6$ alkyl, aryl, alkenyl, or alkynyl, and a functional group having a molecular weight less than or equal to about 100,000 daltons;

n is an integer ranging from 1 to 4; and

R$_{20}$ is an unsubstituted or substituted C$_{1-6}$alkyl.

13. A method of treating opthamological, dermatological, gynecological, urological, and cardiovascular disorders and for hair removal by treating an animal or human host with an effective amount of a compound of claim 1, or a pharmaceutically acceptable salt, solvate, prodrug, or metabolite thereof.

14. A method of treating opthamological, dermatological, gynecological, urological, and cardiovascular disorders and for hair removal by treating an animal or human host with an effective amount of a compound of claim 2, or a pharmaceutically acceptable salt, solvate, prodrug, or metabolite thereof.

15. A method of treating opthamological, dermatological, gynecological, urological, and cardiovascular disorders and for hair removal by treating an animal or human host with an effective amount of a compound of claim 3, or a pharmaceutically acceptable salt, solvate, prodrug, or metabolite thereof.

16. The method of claim 13, wherein the disorders are age-related macular degeneration, choroidal neovascularization, psoriasis, dysfunctional uterine bleeding, condyloma virus, restenosis, and atherosclerotic plaques.

17. The method of claim 14, wherein the disorders are age-related macular degeneration, choroidal neovascularization, psoriasis, dysfunctional uterine bleeding, condyloma virus, restenosis, and atherosclerotic plaques.

18. The method of claim 15, wherein the disorders are age-related macular degeneration, choroidal neovascularization, psoriasis, dysfunctional uterine bleeding, condyloma virus, restenosis, and atherosclerotic plaques.

19. A method of treating opthamological, dermatological, gynecological, urological, and cardiovascular disorders and for hair removal by treating an animal or human host with an effective amount of a compound of claim 8, or a pharmaceutically acceptable salt, solvate, prodrug, or metabolite thereof.

20. The method of claim 19 wherein the disorders are age-related macular degeneration, choroidal neovascularization, psoriasis, dysfunctional uterine bleeding, condyloma virus, restenosis, and atherosclerotic plaques.

* * * * *

UNITED STATES PATENT AND TRADEMARK OFFICE
CERTIFICATE OF CORRECTION

PATENT NO. : 6,376,483 B1
DATED : April 23, 2002
INVENTOR(S) : Byron C. Robinson It is certified that error appears in the above-identified patent and that said Letters Patent is hereby corrected as shown below:

<u>Column 42,</u>
Lines 54 and 55, "$SO_2N\ (R13)(R14)$" should read -- $SO_2NHR_{13}$, $SO_2N(R_{13})(R_{14})$ --;

<u>Column 43,</u>
Lines 53 and 54, "$(R,\ _{15})+X^-$" should read -- $(R_{15})^+$ --;

<u>Column 44,</u>
Line 54, "$+X^-$" should read -- $^+X$ --;

<u>Column 49,</u>
Line 21, "s from" should read -- selected from --;
Line 28, "$SDO_2NHR_{13}$" should read -- $SO_2NHR_{13}$ --;

<u>Column 50,</u>
Line 4, "$(CH_2)n$" should read -- $(CH_2)_nCONHR_{13}$ --;
Line 7, "$+X$" should read -- $^+X$ --; and
Line 15, "$C_{1-6}alkyl$" should read -- $C_{1-6}\ alkyl$ --.

Signed and Sealed this

Twelfth Day of November, 2002

Attest:

Attesting Officer

JAMES E. ROGAN
*Director of the United States Patent and Trademark Office*